United States Patent [19]
Lin et al.

[11] Patent Number: 6,046,157
[45] Date of Patent: Apr. 4, 2000

[54] MODULATION OF TGF-β BY RECOMBINANT TGF-β TYPE II RECEPTOR POLYPEPTIDES

[75] Inventors: Herbert Y. Lin; Xiao-Fan Wang, both of Cambridge; Robert A. Weinberg; Harvey F. Lodish, both of Brookline, all of Mass.

[73] Assignee: Whitehead Institute for Biomedical Research, Cambridge, Mass.

[21] Appl. No.: 08/446,939

[22] Filed: May 23, 1995

Related U.S. Application Data

[62] Division of application No. 08/311,703, Sep. 23, 1994, which is a continuation of application No. 07/786,063, Oct. 31, 1991, abandoned.

[51] Int. Cl.$^7$ .............................. A61K 38/17; C07K 14/71
[52] U.S. Cl. .................................. 514/2; 514/8; 435/69.1
[58] Field of Search ........................... 514/2, 8; 435/69.1

[56] References Cited

U.S. PATENT DOCUMENTS 5,693,607 12/1997 Segarini et al. ........................... 514/2

FOREIGN PATENT DOCUMENTS 0 369 861 A3 5/1990 European Pat. Off. .

OTHER PUBLICATIONS

Massague, et al., "Cellular Receptors for Type Beta Transforming Growth Factor", *J. Biol. Chem.,* 260(5):2636–2645 (1985).
Massague, J., "Subunit Structure of a High–affinity receptor for Type Beta–transforming Growth Factor", *J. Biol. Chem.,* 260(11):7059–7066 (1985).
Cheifetz, S., et al., "Cellular Distribution of Type I and Type II Receptors for Transforming Growth Factor–Beta*", *J. Biol. Chem.,* 261(21):9972–9978 (1986).
Fanger, B.O., et al., "Structure and Properties of the Cellular Receptor for Transforming Growth Factor Type Beta", *Biochem.,* 25:3083–3091 (1986).
Cheifetz, S., et al., "The Transforming Growth Factor–Beta System, a Complex Pattern of Cross–Reactive Ligands and Receptors", *Cell,* 48:409–415 (1987).
Ignotz, R.A., et al., "Cell Adhesion Protein Receptors as Targets for Transforming Growth Factor–Beta Action", *Cell,* 51:189–197 (1987).
Segarini, P.R., et al., "The High Molecular Weight Receptor to Transforming Growth Factor–Beta Contains Glycosaminoglycan Chains", *J. Biol. Chem.,* 263(17):8366–8370 (1988).
Chiefetz, S., et al., "The Transforming Growth Factor–Beta Receptor Type III is a Membrane Proteoglycan", *J. Biol. Chem.,* 263(32):16984–16991 (1988).
Chiefetz, S., et al., "Transforming Growth Factor–Beta (TGF–Beta) Receptor Proteoglycan", *J. Biol. Chem.,* 264(20):12025–12028 (1989).
Andres, J.L., et al., "Membrane–anchored and Soluble Forms of Betaglycan, a Polymorphic Proteoglycan that Binds Transforming Growth Factor–Beta", *J. Cell. Biol.,* 109:3137–3145. (1989).
Massague, J., "The Transforming Growth Factor–Beta Family", *Annu. Rev. Cell. Biol.,* 6:597–641(1990).
Massague, J., et al., "TGF–Beta Receptors and TGF–Beta Binding Proteoglycans: Recent Progress in Identifying Their Functional Properties", *Ann. NY Acad. Sci.,* 593:59–72 (1990).
Laiho, M., et al., "Responsiveness to Transforming Growth Factor–beta (TGF–Beta) Restored by Genetic Complementation between Cells Defective in TGF–Beta Receptors I & II", *J. Biol. Chem.,* 266(14):9108–9112 (1991).
Lin, H.Y., et al., "Expression Cloning of the TGF–Beta Type II Receptor, a Functional Transmembrane Serine/Threonine Kinase", *Cell,* 68:775–785 (1992).
Wrana, J.L., et al., "TFG–β Signals through a Heteromeric Protein Kinase Receptor Complex", *Cell,* 71, in press., Dec. 11 issue (1992).
O'Grady, P., et al., "Expression of a New Type High Molecular Weight Receptor (Type V Receptor) of Transforming Growth Factor β in Normal and Transformed Cells," *Biochemical and Biophysical Research Communications* 179(1):378–385 (1991).
Lopez–Casillas, F., et al., "Structure and Expression of the Membrane Proteoglycan Betaglycan, a Component of the TGF–β Receptor System," *Cell* 67:785–795 (1991).
Wang, X., et al., "Expression Cloning and Characterization of the TGF–β Type III Receptor," *Cell* 67:797–805 (1991).
Cheifetz, S., et al., "Distinct Transforming Growth Factor–β (TGF–β) Receptor Subsets as Determinants of Cellular Responsiveness to Three TGF–β Isoforms," *The Journal of Biological Chemistry* 265(33):20533–20538 (1990).
Cheifetz, S., et al., "The Transforming Growth Factor–β Receptor Type III Is a Membrane Proteoglycan," *J. of Biol. Chem.* 263(32):16984–16991 (1988).
Massague, J., et al., "TGF–β Receptors and TGF–β Binding Proteoglycans: Recent Progress in Identifying Their Functional Properties," *Annals of the N.Y. Acad. of Sci.* 593:59–72 (1990).

*Primary Examiner*—David L. Fitzgerald
*Attorney, Agent, or Firm*—Hamilton, Brook, Smith & Reynolds, P.C.

[57] ABSTRACT

The mammalian TGF-β type II receptor has been cloned. Recombinant TGF-β-binding receptor polypeptides are useful to alter the binding of TGF-β to its receptors and to modulate the effects of TGF-β in vivo.

21 Claims, 3 Drawing Sheets

```
                                                                    -180
-240
CAGGAGGTGAAAGTCCCCGGCGGTCCGGATGGCGCAGTTGCACTGCGCTGCTGAGCTCGC        -180
GGCCGCCTGCGCACACTGGGGGGACTCGCTTCGGCTAGTAACTCCTCCACCTCGCGGCGG        -120
ACGACCGGTCCTGGACACGCTGCCTGCGAGGCAAGTTGAACAGTGCAGAGAAGGATCTTA         -60
AAGCTACACCCGACTTGCCACGATTGCCTTCAATCTGAAGAACCAAAGGCTGTTGGAGAG           0
                                   ---
ATGGCAGTGACATCCCACCACATGATCCCGGTGATGGTTGTCCTGATGAGCGCCTGCCTG          60
MetAlaValThrSerHisHisMetIleProValMetValLeuMetSerAlaCysLeu             20

GCCACCGCCGGTCCAGAGCCCAGCACCCGGTGTGAACTGTCACCAATCAACGCCTCTCAC         120
AlaThrAlaGlyProGluProSerThrArgCysGluLeuSerProIleAsnAlaSerHis          40
            ↑                    &                #
CCAGTCCAGGCCTTGATGGAGAGCTTCACCGTTCTGTCTGGCTGTGCCAGCAGAGGCACC         180
ProValGlnAlaLeuMetGluSerPheThrValLeuSerGlyCysAlaSerArgGlyThr          60
                         +              &
ACCGGGCTGCCAAGGGAGGTCCATGTCCTAAACCTCCGAAGTACAGATCAGGGACCAGGC         240
ThrGlyLeuProArgGluValHisValLeuAsnLeuArgSerThrAspGlnGlyProGly          80

CAGCGGCAGAGAGAGGTTACCCTGCACCTGAACCCCATTGCCTCGGTGCACACTCACCAC         300
GlnArgGlnArgGluValThrLeuHisLeuAsnProIleAlaSerValHisThrHisHis         100

AAACCTATCGTGTTCCTGCTCAACTCCCCCCAGCCCCTGGTGTGGCATCTGAAGACGGAG         360
LysProIleValPheLeuLeuAsnSerProGlnProLeuValTrpHisLeuLysThrGlu         120

AGACTGGCCGCTGGTGTCCCCAGACTCTTCCTGGTTTCGGAGGGTTCTGTGGTCCAGTTT         420
ArgLeuAlaAlaGlyValProArgLeuPheLeuValSerGluGlySerValValGlnPhe        140

CCATCAGGAAACTTCTCCTTGACAGCAGAAACAGAGGAAAGGAATTTCCCTCAAGAAAAT         480
ProSerGlyAsnPheSerLeuThrAlaGluThrGluGluArgAsnPheProGlnGluAsn         160
      +        #
GAACATCTCGTGCGCTGGGCCCAAAAGGAATATGGAGCAGTGACTTCGTTCACTGAACTC         540
GluHisLeuValArgTrpAlaGlnLysGluTyrGlyAlaValThrSerPheThrGluLeu         180

AAGATAGCAAGAAACATCTATATTAAAGTGGGAGAAGATCAAGTGTTTCCTCCTACGTGT         600
LysIleAlaArgAsnIleTyrIleLysValGlyGluAspGlnValPheProProThrCys         200
                                                            &
AACATAGGGAAGAATTTCCTCTCACTCAATTACCTTGCCGAGTACCTTCAACCCAAAGCC         660
AsnIleGlyLysAsnPheLeuSerLeuAsnTyrLeuAlaGluTyrLeuGlnProLysAla         220

GCCGAAGGTTGTGTCCTGCCCAGTCAGCCCCATGAAAAGGAAGTACACATCATCGAGTTA         720
AlaGluGlyCysValLeuProSerGlnProHisGluLysGluValHisIleIleGluLeu         240
          &
ATTACCCCCAGCTCGAACCCTTACAGCGCTTTCCAGGTGGATATAATAGTTGACATACGA         780
IleThrProSerSerAsnProTyrSerAlaPheGlnValAspIleIleValAspIleArg         260

CCTGCTCAAGAGGATCCCGAGGTGGTCAAAAACCTTGTCCTGATCTTGAAGTGCAAAAAG         840
ProAlaGlnGluAspProGluValValLysAsnLeuValLeuIleLeuLysCysLysLys         280
                                                            &
TCTGTCAACTGGGTGATCAAGTCTTTTGACGTCAAGGGAAACTTGAAAGTCATTGCTCCC         900
SerValAsnTrpValIleLysSerPheAspValLysGlyAsnLeuLysValIleAlaPro         300

AACAGTATCGGCTTTGGAAAAGAGAGTGAACGATCCATGACAATGACCAAATTGGTAAGA         960
AsnSerIleGlyPheGlyLysGluSerGluArgSerMetThrMetThrLysLeuValArg         320

GATGACATCCCTTCCACCCAAGAGAATCTGATGAAGTGGGCACTGGACAATGGCTACAGG        1020
AspAspIleProSerThrGlnGluAsnLeuMetLysTrpAlaLeuAspAsnGlyTyrArg         340
```

FIGURE 1A

```
CCAGTGACGTCATACACAATGGCTCCCGTGGCTAATAGATTTCATCTTCGGCTTGAGAAC           1080
ProValThrSerTyrThrMetAlaProValAlaAsnArgPheHisLeuArgLeuGluAsn            360

AACGAGGAGATGAGAGATGAGGAAGTCCACACCATTCCTCCTGAGCTTCGTATCCTGCTG           1140
AsnGluGluMetArgAspGluGluValHisThrIleProProGluLeuArg*IleLeuLeu*          380

GACCCTGACCACCCGCCCGCCCTGGACAACCCACTCTTCCCAGGAGAGGGAAGCCCAAAT           1200
*AspProAspHisProProAlaLeu*AspAsnProLeuPheProGlyGluGlySerProAsn          400
       peptide 1
GGTGGTCTCCCCTTTCCATTCCCGGATATCCCCAGGAGAGGCTGGAAGGAGGGCGAAGAT           1260
GlyGlyLeuProPheProPheProAspIleProArgArgGlyTrpLysGluGlyGluAsp            420

AGGATCCCCCGGCCAAAGCAGCCCATCGTTCCAGTGTTCAACTGCTTCCTGACCACCGA            1320
ArgIleProArgProLys*GlnProIleValProSerValGln*LeuLeuProAspHisArg          440
                      peptide 2
GAACCAGAAGAAGTGCAAGGGGCGTGGACATCGCCCTGTCAGTCAAATGTGACCATGAA            1380
GluProGluGluValGlnGlyGlyValAspIleAlaLeuSerValLysCysAspHisGlu            460
                                                          &
AAGATGGTCGTGGCTGTAGACAAAGACTCTTTCCAGACCAATGGCTACTCAGGGATGGAG           1440
LysMetValValAlaValAspLysAspSerPheGlnThrAsnGlyTyrSerGlyMetGlu            480
                                                      +
CTCACCCTGTTGGATCCTTCGTGTAAAGCCAAAATGAATGGTACTCACTTTGTTCTCGAG           1500
LeuThrLeuLeuAspProSerCysLysAlaLysMetAsnGlyThrHisPheValLeuGlu            500
                  &                    #
TCTCCCCTGAATGGCTGTGGTACTCGACATCGGAGGTCGACCCCGGATGGTGTGGTTTAC           1560
SerProLeuAsnGlyCysGlyThrArgHisArgArgSerThrProAspGlyValValTyr            520
                 &
TATAACTCTATTGTGGTGCAGGCTCCGTCCCTGGGGATAGCAGTGGCTGGCCTGATGGC            1620
TyrAsnSerIleValValGlnAlaProSerProGlyAspSerSerGlyTrpProAspGly            540
                                                      +++
TATGAAGACTTGGAGTCAGGCGATAATGGATTTCCTGGAGACGGGGATGAAGGAGAAACT           1680
TyrGluAspLeuGluSerGlyAspAsnGlyPheProGlyAspGlyAspGluGlyGluThr            560

GCCCCCCTGAGCCGAGCTGGAGTGGTGGTGTTTAACTGCAGCTTGCGGCAGCTGAGGAAT          1740
AlaProLeuSerArgAlaGlyValValValPheAsnCysSerLeuArgGlnLeuArgAsn            580
                                        #    &
CCCAGTGGCTTCCAGGGCCAGCTCGATGGAAATGCTACCTTCAACATGGAGCTGTATAAC           1800
ProSerGlyPheGlnGlyGlnLeuAspGlyAsnAlaThrPheAsnMetGluLeuTyrAsn            600
                                    #
ACAGACCTCTTTCTGGTGCCCTCCCCAGGGGTCTTCTCTGTGGCAGAGAACGAGCATGTT           1860
ThrAspLeuPheLeuValProSerProGlyValPheSerValAlaGluAsnGluHisVal            620

TATGTTGAGGTGTCTGTCACCAAGGCTGACCAAGATCTGGGATTCGCCATCCAAACCTGC           1920
TyrValGluValSerValThrLysAlaAspGlnAspLeuGlyPheAlaIleGlnThrCys            640
                                                     &
TTTCTCTCTCCATACTCCAACCCAGACAGAATGTCTGATTACACCATCATCGAGAACATC           1980
PheLeuSerProTyrSerAsnProAspArgMetSerAspTyrThrIleIleGluAsnIle            660

TGTCCGAAAGACGACTCTGTGAAGTTCTACAGCTCCAAGAGAGTGCACTTTCCCATCCCG           2040
CysProLysAspAspSerValLysPheTyrSerSerLysArgValHisPheProIlePro            680
&
CATGCTGAGGTGGACAAGAAGCGCTTCAGCTTCCTGTTCAAGTCTGTGTTCAACACCTCC           2100
HisAlaGluValAspLysLysArgPheSerPheLeuPheLysSerValPheAsnThrSer            700
                                                         #
CTGCTCTTCCTGCACTGCGAGTTGACTCTGTGCTCCAGGAAGAAGGGCTCCCTGAAGCTG           2160
LeuLeuPheLeuHisCysGluLeuThrLeuCysSerArgLysLysGlySerLeuLysLeu            720
                &                        &
```

FIGURE 1B

```
CCGAGGTGTGTGACTCCTGACGACGCCTGCACTTCTCTCGATGCCACCATGATCTGGACC            2220
ProArgCysValThrProAspAspAlaCysThrSerLeuAspAlaThrMetIleTrpThr              740
                        &                                   &
ATGATGCAGAATAAGAAGACATTCACCAAGCCCCTGGCTGTGGTCCTCCAGGTAGACTAT            2280
MetMetGlnAsnLysLysThrPheThrLysProLeuAlaValValLeuGlnValAspTyr             760

AAAGAAAATGTTCCCAGCACTAAGGATTCCAGTCCAATTCCTCCTCCTCCTCCACAGATT            2340
LysGluAsnValProSerThrLysAspSerSerProIleProProProProProGlnIle             780

TTCCATGGCCTGGACACGCTCACCGTGATGGGCATTGCATTTGCAGCATTTGTGATCGGA            2400
PheHisGlyLeuAspThrLeuThrValMetGlyIleAlaPheAlaAlaPheValIleGly             800

GCGCTCCTGACGGGGGCCTTGTGGTACATCTACTCCCACACAGGGGAGACAGCACGAAGG            2460
AlaLeuLeuThrGlyAlaLeuTrpTyrIleTyrSerHisThrGlyGluThrAlaArgArg             840
                                          $     @
CAGCAAGTCCCTACCTCGCCGCCAGCCTCGGAGAACAGCAGCGCGGCCCACAGCATCGGC            2520
GlnGlnValProThrSerProProAlaSerGluAsnSerSerAlaAlaHisSerIleGly             860

AGCACTCAGAGTACCCCCTGCTCTAGCAGCAGCACAGCCTAGGTGGACAGACAGACGCCC            2580
SerThrGlnSerThrProCysSerSerSerSerThrAla                                  873

GCCCACCGCAGCCAGGGCAGGGCCCGATGCCAGTGCTGCGTGTCCACAGTCAGAAGTCTT            2640
GATCTGGGCTCCCTGTAAAGAAAGAGTGAATTTCAGTATACAGACAGCCAGTTCTACCCA            2700
CCCCTTACCACGGCCCACATAAATGTGACCCTGGGCATCTGTCACACGAAAGCTAAGCTG            2760
GTGGCCTTCCCCACCAGCCCCTCGCAGGATGGGGTTTCAATGTGAAACATCTGCCAGTT            2820
TTGTTTTGTTTTTTTAATGCTGCTTTGTCCAGGTGTCCAAACATCCATCATTTGGGGTGG            2880
TCTGTTTTACAGAGTAAAGGAGGCGGTGAAGGGACGTCAGCTAGTGTGTAGAGCCAAGGG            2940
GAGACAGCTAGGATTCTCGCCTAGCTGAACCAAGGTGTAAAATAGAAGCACGCTCC                2997
```

FIGURE 1C

MODULATION OF TGF-β BY RECOMBINANT TGF-β TYPE II RECEPTOR POLYPEPTIDES

This application is a division of application Ser. No. 08/311,703 filed Sep. 23, 1994 which is a File Wrapper Continuation of 07/786,063, filed Oct. 31, 1991, now abandoned.

FUNDING

Work described herein was funded by National Cancer Institute Grant No. R35-CA39826; National Heart, Lung and Blood Institute Centers of Excellence Grant HL-41484; the Damon Runyon-Walter Winchell Cancer Research Fund; National Institutes of Health predoctoral training grant number T 32 BM07287-16; and the American Cancer Society. The United States government has certain rights in the invention.

BACKGROUND

Transforming growth factor-beta (TGF-β) is a member of a family of structurally related cytokines that elicit a variety of responses, including growth, differentiation, and morphogenesis, in many different cell types. (Roberts, A. B. and H. B. Sporn, In: *Peptide Growth Factors and Their Receptors*, Springer-Verlag, Heidelberg, pp. 421–472 (1990); Massague, J., *Annu. Rev. Cell. Biol.* 6: 597–641 (1990)) In vertebrates at least five different forms of TGF-β, termed TGF-β1 to TGF-β5, have been identified; they all share a high degree (60%–80%) of amino-acid sequence identity. While TGF-β1 was initially characterized by its ability to induce anchorage-independent growth of normal rat kidney cells, its effects on most cell types are antimitogenic. (Altschul, S. F. et al., *J. Mol. Biol.* 215: 403–410 (1990); Andres, J. L. et al., *J. Cell. Biol.* 109: 3137–3145 (1989)) It is strongly growth-inhibitory for many types of cells, including both normal and transformed epithelial, endothelial, fibroblast, neuronal, lymphoid, and hematopoietic cells. In addition, TGF-β plays a central role in regulating the formation of extracellular matrix and cell-matrix adhesion processes.

In spite of its widespread effects on cell phenotype and physiology, little is known about the biochemical mechanisms that enable TGF-β family members to elicit these varied responses. Three distinct high-affinity cell-surface TGF-β-binding proteins, termed type I, II and III, have been identified by incubating cells with radiolabelled TGF-β1, cross-linking bound TGF-β1 to cell surface molecules, and analyzing the labelled complexes by polyacrylamide gel electrophoresis. (Massague, J. and B. Like, *J. Biol. Chem.* 260: 2636–2645 (1985); Cheifetz, S. et al. *J. Biol. Chem.* 261: 9972–9978 (1986).) The binding constants are about 5–50 pM for the type I and II receptor and 30–300 pM for the type III receptor. (Boyd, F. T. and J. Massague, *J. Biol. Chem.* 264: 2272–2278 (1989))

The type I and II receptors, of estimated 53 and 70–100 kilodaltons mass respectively, are N-glycosylated transmembrane proteins that are similar in many respects. Each of these receptors has a distinct affinity for each member of the TGF-β family of ligands. (Boyd, F. T. and J. Massague, *J. Biol. Chem.* 264: 2272–2278 (1989)) In contrast, the type III receptor shows comparable affinities for all TGF-β isotypes; the type III receptor is the most abundant cell-surface receptor for TGF-β in many cell lines (upwards of 200,000 per cell), and is an integral membrane proteoglycan. It is heavily modified by glycosaminoglycan (GAG) groups, and migrates heterogeneously upon gel electrophoresis as proteins of 280 to 330 kilodaltons. When deglycosylated with heparitinase and chondrontinase, the protein core migrates as a 100–110 kilodalton protein. The TGF-β binding site resides in this protein core, as non glycosylated forms of this receptor that are produced in cell mutants defective in GAG synthesis are capable of ligand binding with affinities comparable to those of the natural receptor. (Cheifetz, S. and J. Massague, *J. Biol. Chem.*, 264: 12025–12028 (1989) A variant form of type III receptor is secreted by some types of cells as a soluble molecule that apparently lacks a membrane anchor. This soluble species is found in low amounts in serum and in extracellular matrix.

The type III receptor, also called betaglycan, has a biological function distinct from that of the type I and II receptors. Some mutant mink lung epithelial cell (Mv1Lu) selected for loss of TGF-β responsiveness no longer express type I receptors; others, similarly selected, lose expression of both the type I and II receptors. However, all these variants continue to express the type III receptor. (Boyd, F. T. and J. Hassague, *J. Biol. Chem.* 264: 2272–2278 (1989); Laiho, M. et al., J. Biol. Chem. 265: 18518–18524 (1990)) This has led to the proposal that types I and II receptors are signal-transducing molecules while the type III receptor, may subserve some other function, such as in concentrating ligand before presentation to the bona fide signal-transducing receptors. The secreted form of type III receptor, on the other hand, may act as a reservoir or clearance system for bioactive TGF-β.

Additional information about-each of these TGF-β receptor types would enhance our understanding of their roles and make it possible, if desired, to alter their functions.

SUMMARY OF THE INVENTION

The present invention relates to isolation, sequencing and characterization of DNA encoding the TGF-β type III receptor of mammalian origin and DNA encoding the TGF-β type II receptor of mammalian origin. It also relates to the encoded TGF-β type III and type II receptors, as well as to the soluble form of each; uses of the receptor-encoding genes and of the receptors themselves; antibodies specific for TGF-β type III receptor and antibodies specific for TGF-β type II receptor. In particular, it relates to DNA encoding the TGF-β type III receptor of rat and human origin, DNA encoding the TGF-β type II receptor of human origin and homologous of each.

The TGF-β receptor-encoding DNA of the present invention can be used-to identify equivalent TGF-β receptor type III and type II genes from other sources, using, for example, known hybridization-based methods or the polymerase chain reaction. The type III receptor gene, the type II receptor gene or their respective encoded products can be used to alter the effects of TGF-β (e.g., by altering receptivity of cells to TGF-β or interfering with binding of TGF-β to its receptor), such as its effects on cell proliferation or growth, cell adhesion and cell phenotype. For example, the TGF-β receptor type III gene, the TGF-β receptor type II gene, or a truncated gene which encodes less than the entire receptor (e.g., soluble TGF-β type III receptor, soluble TGF-β type II receptor or the TGF-β type III or type II binding site) can be administered to an individual in whom TGF-β effects are to be altered. Alternatively, the TGF-β type III receptor, the TGF-β type II receptor, a soluble form thereof (i.e., a form lacking the membrane anchor) or an active binding site of the TGF-β type III or the type II receptor can be administered to an individual to alter the effects of TGF-β.

Because of the many roles TGF-β has in the body, availability of the TGF-β receptors described herein makes it possible to further assess TGF-β function and to alter (enhance or diminish) its effects.

BRIEF DESCRIPTION OF THE DRAWINGS

FIGS. 1A–1C (SEQ ID NOS: 5 and 6) is the DNA sequence and the translated amino acid sequence of type III TGF-β1 receptor cDNA clone R3-OFF (full insert size 6 kb), in which the open reading frame with flanking sequences of the clone are shown. The transmembrane domain is indicated by a single underline. Peptide sequences from purified type III receptor, mentioned in text, that correspond to the derived sequence, are in italics and underlined. Potential N-linked glycosylation sites are indicated by #, and extracellular cysteines by &. A consensus protein kinase C phosphorylation site is indicated by $. The last non-vectorencoded amino acid of Clone R3-OF (2.9 kb) is indicated by @. Consensus proteoglycan attachment site is indicated by +++. Other potential glycosaminoglycan attachment sites are indicated by +. The upstream in-frame stop codon (−42 to −44) is indicated by a wavy line. Signal peptide cleavage site predicted by vonHeijne's algorithm (von Heijne, G., *Nucl. Acid. Res.* 14: 4683–4690 (1986) is indicated by an arrow.

DETAILED DESCRIPTION OF THE INVENTION

The subject invention is based on the isolation and sequencing of DNA of vertebrate, particularly mammalian, origin which encodes TGF-β type III receptor and DNA of mammalian origin which encodes TGF-β type II receptor, expression of the encoded products and characterization of the expressed products. As described, a full-length cDNA which encodes TGF-β receptor type III has been isolated from a cDNA library constructed from a rat vascular smooth muscle cell line and a full-length cDNA which encodes TGF-β type II receptor has been isolated from a human cDNA library. The human homologue of the type III gene has also been cloned. A deposit of human TGF-β type III cDNA in the plasmid pBSK has been made under the terms of the Budapest Treaty at the American Type Culture Collection (Oct. 21, 1991) under Accession Number 75127. All restrictions upon the availability of the deposited material will be irrevocably removed upon granting of a U.S. patent based on the subject application.

Isolation and Characterization of TGF-β Type III Receptor

As described herein, two separate strategies were pursued for the isolation of the TGF-β type III receptor cDNA. In one approach, monoclonal antibodies were generated against the type III receptor protein and used to purify the receptor, which was then subjected to microsequencing. (See Example 1) Microsequencing of several peptides resulting from partial proteolysis of the purified receptor produced four oligopeptide sequences, which were used to construct degenerate oligonucleotides. The degenerate oligonucleotides were used either as primers in a cloning strategy using the polymerase chain reaction (PCR) or as probes in screening cDNA libraries. Although this strategy did not prove to be productive, the oligopeptide sequences were useful in verifying the identity of the receptor clones isolated by the second strategy.

In the second approach to isolating TGF-β receptor-encoding clones, an expression cloning strategy was used in COS cells; direct visualization of receptor positive cells was used to isolate receptor cDNAs. (See Example 2) In this approach, a cDNA library was constructed from A-10 cells, a rat vascular smooth muscle cell line which expresses all three TGF-β receptors (type I, II and III). COS cells transfected with cDNA components of this library in a vector carrying the cytomegalovirus (CMV) transcriptional promoter and the SV40 origin of replication were screened to identify cells expressing substantially higher than normal levels of TGF-β receptor. One transfectant expressing such high levels of a TGF-β binding protein was identified and the original pool of expression constructs from which it was derived was split into subpools, which were subjected to a second round of screening. Two further rounds of sib-selection resulted in isolation of one cDNA clone (R3-OF) with a 2.9 kb insert which induced high levels of TGF-β-binding proteins in approximately 10% of cells into which it was introduced. The specificity of the TGF-β binding was validated by showing that addition of a 200-fold excess unlabeled competitor TGF-β1 strongly reduced binding of 125 I-TGF-β to transfected cells.

The R3-OF cDNA encoded an open reading frame of 817 amino acid residues, but did not contain a stop codon. R3-OF was used as a probe to isolate a full-length cDNA from a rat 208F library. The resulting clone, R3-OFF, is 6 kb in length and encodes a protein of 853 amino acids, which is colinear with clone R3-OF. The nucleotide sequence of R3-OFF is shown in FIGS. 1A–1C, along with the translated amino acid sequence.

Characterization of the receptor encoded by R3-OFF was carried out, as described in Example 3. Results showed three distinct TGF-β binding protein species of TGF-β on the surface of mock-transfected COS cells, which is in accord with results reported by others. (Massague, J. et al., *Ann. NY Acad. Sci.* 593: 59–72 (1990)). These included the two lower molecular weight type I and II receptors (65 and 85 kD) and the higher molecular weight type III proteoglycan, which migrates as a diffuse band of 280–330 kd. Enzymatic removal of the proteoglycan yielded a core protein of approximately 100 kd. Binding to all three receptor types is specific in that it was competed by 200-fold excess of unlabeled TGF-β1.

Transfecting the isolated cDNA caused a two-fold increase in expression of the type III receptor. When a cell lysate derived from COS cells transfected with clone R3-OFF was treated with deglycosylating enzymes, the heterogeneous 280–330 kd band was converted to a protein core which co-migrates with the type III protein core seen in parental A10 cells. Importantly, the recombinant protein core migrated differently from the endogenous COS cell type III protein core.

These observations were confirmed and extended using stably transfected cells expressing the type III cDNA. L6 rat skeleton muscle myoblasts do not express any detectable type III mRNA and no endogeneous surface type III receptor (Massague et al., 1986; Segarini et al., 1989). These cells were transfected with the isolated cDNA in the vector pcDNA-neo. Cell clones stably expressing this clone in both the forward and reverse orientations with respect to the CMV promoter were isolated and analyzed by ligand binding assay.

Introduction of either the full-length clone R3-OFF or the partial clone R3-OF in the forward orientation resulted in expression of type III receptor. L6 cells transfected with the cDNA clones in the reverse orientation did not express this protein. Importantly, the apparent size of the protein core of the type III receptor in cells transformed with the R3-OF clone is smaller than that from R3-OFF transformed cells, consistent with the difference in the sizes of the protein cores predicted from their nucleic acid sequences.

Surprisingly, binding of radio-labeled ligand to the type II receptor was increased by 2.5 fold in cells expressing the type III cDNA. Binding to the type I receptor was unchanged. This apparently specific up-regulation of ligand-binding to the type II receptor was evident in all of the 15 stably transfected L6 cell lines analyzed to date. Furthermore, this effect seems to be mediated equally well by the full-length clone or a truncated clone (R3-OF) that lacks the cytoplasmic domain of TGF-β type III receptor was expressed.

Expression of type III receptor mRNA was assessed by Northern blot analysis and RNA blot analysis. Northern gel analysis showed that the type III receptor mRNA is expressed as a single 6 kb message in several rat tissues. RNA dot blot analysis of several different tissue culture cell lines was also carried out. Cells of mouse origin (MEL and YH16) appear to express a smaller (~5.5 kb) message for the type III mRNA than those of pig, rat and human origin. In all of these cells, expression or absence of the type III mRNA is consistent with the expression or absence of detectable cell surface type III receptors, with the notable exception of the retinoblastoma cell lines (Y79, Weri-1, Weri-24, and Weri-27). These cells lack detectable surface expression of type III receptor, which confirms an earlier report. (Kimchi, A. et al., Science 240: 196–198 (1988)). It is striking that the type III receptor MRNA is expressed in these cells at a level comparable to that of other cells that do indeed express type III receptor proteins at readily detectable levels. It appears that TGF-β receptor III expression, which is substantial in normal retinoblasts (AD12), has been down-regulated in these retinoblastoma tumor cells, perhaps through post-transcriptional mechanisms.

The nucleotide sequence full reading frame along with flanking sequences of the full-length cDNA clone R3-OFF was determined and is presented in FIGS. 1A–1C. The reading frame encodes a protein of 853 amino acid residues, which is compatible with the 100 kD size observed for the fully deglycosylated TGF-β1 type III receptor. The identity of the receptor as TGF-β type III was verified by searching for segments of the putative transcription product which included the peptide sequences determined by microsequencing of the isolated type III receptor. (See Example 1) As indicated in FIGS. 1A–1C, two segments of derived protein (underlined and italicized, residues 378–388 and 427–434) precisely match with the amino acid sequences of two peptides (I and III) determined from direct biochemical analysis of the purified type III receptor.

Further analysis showed that TGF-β type III binding protein has an unusual structure for a cytokine receptor. Hydropathy analysis indicates that the protein includes a N-terminal signal sequence, followed by a long, hydrophilic N-terminal region. A 27 residue region of strong hydrophobicity (underlined in FIGS. 1A–1C, residues 786–812) toward the C-terminus represents the single putative transmembrane domain. This suggests that nearly all of the receptor which is an N-terminal extracellular domain is anchored to the plasma membrane near its C-terminus. A relatively small C-terminal tail of 41 residues represents the cytoplasmic domain.

Analysis of related sequences provides few clues to function of TGF-β type III protein. Only one other gene described to date, a glycoprotein expressed in high quantities by endothelial cells and termed endoglin, contains a related amino acid sequence. The most homologous regions between the sequences of the type III receptor and endoglin (74%) falls primarily in the putative transmembrane and cytoplasmic domains. Similar to the general structure of type III receptor, endoglin is a glycoprotein which contains a large hydrophilic N-terminal domain which is presumably extracellular, followed by a putative transmembrane domain and a short cytoplasmic tail of 47 amino acid residues. The biological role of endoglin is still unclear at present, although it has been suggested that it may involved in cell-cell recognition through interactions of an "RGD" sequence on its ectodomain with other adhesion molecules. Unlike the TGF-β type III receptor, endoglin does not carry GAG groups.

Isolation of TGF-β Type II Receptor

The cDNA encoding the type II TGF-β receptor was also isolated, using expression cloning in COS cells. A full-length cDNA (designated clone 3FF) was isolated by high stringency hybridization from a human HepG2 cell cDNA library. Analysis showed that the corresponding message is a 5 kb message which is expressed in different cell lines and tissues. Sequence analysis indicated that the cDNA has an open reading frame encoding a core 567 amino acid residue protein. The nucleotide sequence of the full-length type II TGF-β receptor cDNA clone 3FF is shown in SEQ ID NO: 7; the amino acid sequence is represented in SEQ ID NO: 8.

The 567 amino acid residue protein has a single putative transmembrane domain, several consensus glycosylation sites, and a putative intracellular serine/threonine kinase domain. The predicted size of the encoded protein core is ~60 kd, which is too large for a type I TGF-β receptor. Instead, crosslinking experiments using iodinated TGF-β and COS cells transiently transfected with clone 3FF shows over-expression of a protein approximately 70–80 kd which corresponds to the size of type II TGF-β receptors. Thus, clone 3FF encodes a protein that specifically binds TGF-β and has an expressed protein size of 70–80 kd, both characteristic of the type II TGF-β receptor.

Plasmid 3FF was deposited in accordance with the provisions of the Budapest Treaty at the American Type Cilture Collection (ATCC), 12301 Parklawn Drive, Rockville, Md. 20852, U.S.A. on Nov. 12, 1997, and assigned Accession Number ATCC 209455.

Uses of the Cloned TGF-β Receptors and Related Products

For the first time, as a result of the work described herein, DNAs encoding two of the three high affinity cell-surface TGF-β receptors have been isolated, their sequences and expression patterns determined and the encoded proteins characterized. Expression of the TGF-β type III receptor in cells which do not normally express the receptor, followed by ligand binding assay, verified that the cloned type III receptor-encoding DNA (i.e., either the full-length clone R3-OFF or the partial clone R3-OF) encoded the receptor. In addition, the work described herein resulted in the surprising finding that binding of TGF-β to type II receptors in cells expressing the type III DNA was increased by 2.5 fold.

Additional insight into the role of the TGF-β type III receptor and its interaction with TGF-β type II receptor is a result of the work described. For example, the role of TGF-β type III receptor is unclear, but it has been proposed that it serves a most unusual function of attracting and concentrating TGF-βs for eventual transfer to closely situated signal-transducing receptors. While most cytokines bind to a single cell surface receptor, members of the TGF-β family bind with greater or lesser affinity to three distinct cell surface proteins. This has raised the question of why these three receptors are displayed by most cell types and whether they subserve distinct functions. Evidence obtained to date suggests that the type III receptor may perform functions quite different from those of types I and II. Thus, type III is substantially modified by GAGs while types I and II appear to carry primarily the N-linked (and perhaps O-linked) sidechains that are characteristic of most growth factor receptors. In addition, variant cells that have been selected for their ability to resist TGF-β-induced growth inhibition show the absence of Type I or Type II receptors while continuing to display Type III receptors. Together, these data have caused some to propose that the Type I and II receptors represent bona fide signal-transducing receptors while the type III receptor, described here, plays another distinct role in the cell.

It remains possible that the type III receptor serves a most unusual function of attracting and concentrating TGF-βs on the cell surface for eventual transfer to closely situated signal-transducing receptors. Such a function would be unprecedented for a proteinaceous receptor, although heparin sulfate has been shown to activate basic FGF by binding to this growth factor prior to FGF association with its receptor (Yayon, A. et al., *Cell* 64: 841–848 (1991)) Parenthetically, since the type III receptor also contains large quantities of heparan sulfate side-chains, it may also bind and present basic FGF to its receptor.

Evidence that is consistent with the role for the type III receptor comes from the work with L6 rat myoblast cells which is described herein. As described above, in L6 cells overexpressing type III receptor, the binding of radiolabelled TGF-β to the type II receptor is increased several fold when compared with that seen with parental cells. Further assessment of TGF-β type III function and interaction with type II and type I receptors will be needed to answer these questions and can be carried out using the materials and methods described here.

TGF-β receptors, both type III and type II, can be identified in other species, using all or a portion of the DNA encoding the receptor to be identified as a probe and methods described herein. For example, all or a portion of the DNA sequence encoding TGF-β type III receptor (shown in FIGS. 1A–1C) or all or a portion of the DNA sequence encoding TGF-β type II receptor (shown in SEQ ID NO: 7) can be used to identify equivalent sequences in other animals. Stringency conditions used can be varied, as needed, to identify equivalent sequences in other species. Once a putative TGF-β receptor type III or type II-encoding sequence has been identified, whether it encodes the respective receptor type can be determined using known methods, such as described herein for verification that the cDNA insert of full-length clone R3-OFF and the cDNA insert of partial clone R3-OF encode the type III receptor. For example, DNA isolated in this manner can be expressed in an appropriate host cell which does not express the receptor mRNA or the surface receptor (e.g., L6 rat skeleton muscle myoblasts) and analyzed by ligand binding (TGF-β binding) assay, as described herein.

Also as a result of the work described herein, antibodies (polyclonal or monoclonal) specific for the cloned TGF-β type III or the clones TGF-β type II receptor can be produced, using known methods. Such antibodies and host cells (e.g., hybridoma cells) producing the antibodies are also the subject of the present invention. Antibodies specific for the cloned TGF-β receptor can be used to identify host cells expressing isolated DNA thought to encode a TGF-β receptor. In addition, antibodies can be used to block or inhibit TGF-β activity. For example, antibodies specific for the cloned TGF-β type III receptor can be used to block binding of TGF-β to the receptor. They can be administered to an individual for whom reduction of TGF-β binding is desirable, such as in some fibrotic disease (e.g., of skin, kidney and lung).

DNA and RNA encoding TGF-β type III receptor and DNA and RNA encoding TGF-β type II receptor are now available. As used herein, the term DNA or RNA encoding the respective TGF-β receptor includes any oligodeoxynucleotide or oligodeoxyribonucleotide sequence which, upon expression, results in production of a TGF-β receptor having the functional characteristics of the TGF-β receptor. That is, the present invention includes DNA and RNA which, upon expression in an appropriate host cell, produces a TGF-β type III receptor which has an affinity for TGF-β similar to that of the TGF-β type III receptor on naturally occurring cell surfaces (e.g., it shows comparable affinities for all TGF-β isotypes). Similarly, the present invention includes DNA and RNA which, upon expression in an appropriate host cell, produces a TGF-β type II receptor which has an affinity for TGF-β similar to that of TGF-β type II receptor on naturally occurring cell surfaces (e.g., it has a distinctive affinity for each member of the TGF-β family of ligands similar to that of the naturally occurring TGF-β type II receptor). The DNA or RNA can be produced in an appropriate host cell or can be produced synthetically (e.g., by an amplification technique such as PCR) or chemically.

The present invention also includes the isolated TGF-β type III receptor encoded by the nucleotide sequence of full-length R3-OFF, the isolated TGF-β type III receptor encoded by the nucleotide sequence of partial clone R3-OF, the isolated TGF-β type II receptor encoded by the nucleotide sequence of full-length clone 3FF and TGF-β type III and type II receptors which bind TGF-β isotypes with substantially the same affinity. The isolated TGF-β type III and type II receptors can be produced by recombinant techniques, as described herein, or can be isolated from sources in which they occur naturally or synthesized chemically. As used herein, the terms cloned TGF-β type III and cloned TGF-β type II receptors include the respective receptors identified as described herein, and TGF-β type III and type II receptors (e.g., from other species) which exhibit substantially the same affinity for the TGF-β isotypes as the respective receptors.

As described previously, cells in which the cloned TGF-β type III receptor is expressed bind TGF-β in essentially the same manner as do cells on which the type III receptor occurs naturally. Further analysis of ligand interactions with the cloned TGF-β type III receptor, based upon site-directed mutagenesis of both TGF-β and the receptor, can be carried out to identify residues important for binding. For example, DNA having the sequence of FIGS. 1A–1C can be altered by adding, deleting or substituting at least one nucleotide, in order to produce a modified DNA sequence which encodes a modified cloned TGF-β type III receptor. The functional characteristics of the modified receptor (e.g., its TGF-β-binding ability and association of the binding with effects normally resulting from binding) can be assessed, using the methods described herein. Modification of the cloned TGF-β type III receptor can be carried out to produce, for example, a form of the TGF-β type III receptor, referred to herein as soluble TGF-β receptor, which is not membrane bound and retains the ability to bind the TGF-β isotypes with an affinity substantially the same as the naturally-occurring receptor. Such a TGF-β type III receptor could be produced, using known genetic engineering or synthetic techniques; it could include none of the transmembrane region present in the naturally-occurring TGF-β type III receptor or only a small portion of that region (i.e., small enough not to interfere with its soluble nature). For example, it can include amino acids 1 through 785 of the TGF-β type III sequence of FIGS. 1A–1C or a portion of that sequence sufficient to retain TGF-β binding ability (e.g., amino acids 24–785, which does not include the signal peptide cleavage site present in the first 23 amino acids). A soluble TGF-β type II receptor (e.g., one which does not include the transmembrane and cytoplasmic domains) can also be produced. For example, it can include amino acids 1 through 166, inclusive, of SEQ ID NO: 8 or a sufficient portion thereof to retain TGF-β binding ability substantially the same as that of TGF-β type II receptor.

The TGF-β type III receptor and/or type II receptor can be used for therapeutic purposes. As described above, the TGF-β family of proteins mediate a wide variety of cellular activities, including regulation of cell growth, regulation of cell differentiation and control of cell metabolism. TGF-β may be essential to cell function and most cells synthesize TGF-β and have TGF-β cell surface receptors. Depending on cell type and environment, the effects of TGF-β vary: proliferation can be stimulated or inhibited, differentiation can be induced or interrupted and cell functions can be stimulated or suppressed. TGF-β is present from embryonic stages through adult life and, thus, can affect these key processes throughout life. The similarities of a particular TGF-β (e.g., TGF-β1) across species and from cell to cell are considerable. For example, the amino acid sequence of a particular TGF-β and the nucleotide sequence of the gene which encodes it regardless of source, are essentially identical across species. This further suggests that TGF-β has a critical role in essential processes.

Specifically, TGF-β has been shown to have anti-inflammatory and immune suppression capabilities, to play an important role in bone formation (by increasing osteoblast activity), inhibit cancer cell proliferation in culture, and control proliferation of glandular cells of the prostate. As a result, it has potential therapeutic applications in altering certain immune system responses (and possibly in modifying immune-mediated diseases); in treating systemic bone disease (e.g., osteoporosis) and conditions in which bone growth is to be enhanced (e.g., repair of broken bones) and in controlling growth and metastasis of cancer cells. In addition, TGF-β appears to play a role in determining whether some cell types undergo or do not undergo mitosis. In this respect, TGF-β may play an important role in tissue repair. Some diseases or conditions appear to involve low production or chronic overproduction of TGF-β. (For example, results of animal studies suggest that there is a correlation between the over production of TGF-β and diseases characterized by fibrosis in the lung, kidney, liver or in viral mediated immune expression.)

Clearly, TGF-β has key roles in body processes and numerous related potential clinical or therapeutic applications in wound healing, cancer, immune therapy and bone therapy. Availability of TGF-β receptor genes, the encoded products and methods of using them in vitro and in vivo provides an additional ability to control or regulate TGF-β activity and effect in the body. For example, the TGF-β type II or type III receptor encoded by the type II or the type III receptor genes of the subject invention can be used, as appropriate, to alter the effects of TGF-β (e.g., to enhance the effect of TGF-β in the body or to inhibit or reduce (totally or partially) its effects). It is also possible to administer to an individual in whom TGF-β bound to TGF-β type III receptor, such as soluble TGF-β type III receptor. The present invention provides both a TGF-β agonist and a TGF-β antagonist. For these purposes, DNA gene encoding the entire TGF-β type II or type III receptor, the encoded type II or type III receptor or a soluble form of either receptor can be used. Alternatively, antibodies or other ligands designed based upon these sequences or specific for them can be used for this purpose.

Knowledge of the amino acid sequences of TGF-β type III and type II receptors makes it possible to better understand their structure and to design compounds which interfere with binding of the receptor with TGF-β. It makes possible identification of existing compounds and design of new compounds which are type III and/or type II receptor antagonists.

Cells expressing the type III and/or type II receptors of the present invention can be used to screen compounds for their ability to interfere with (block totally or partially) TGF binding to the receptors. For example, cells which do not express TGF-β type III receptor (e.g., L6 rat skeleton muscle myoblasts) but have been modified to do so by incorporation of the type III cDNA in an appropriate vector can be used for this purpose. A compound to be assessed is added, for example, to tissue culture dishes containing type III expressing cells, along with labeled TGF-β. As a control, the same concentration of labeled TGF-β is added to tissue culture dishes containing the same type of cells. After sufficient time for binding of TGF-β to the receptor to occur, binding of labeled TGF-β to the cells is assessed, using known methods (e.g., by means of a gamma counter) and the extent to which it occurred in the presence and in the absence of the compound to be assessed is determined. Comparison of the two values show whether the test compound blocked TGF-β binding to the receptor (i.e., less binding in the presence of the compound than in its absence is evidence that the test compound has blocked binding of TGF-β to the TGF-β type III receptor).

Alternatively, a cell line expressing the TGF-β receptor or cells expressing microinjected TGF-β receptor RNA, can be used to assess compounds for their ability to block TGF-β binding to the receptor. In this embodiment, a compound to be assessed is added to tissue culture dishes containing the cell line cells expressing microinjected TGF-β receptor RNA, along with TGF-β. As a control, TGF-β alone is added to the same type of cells expressing microinjected endothelin receptor RNA. After sufficient time for binding of TGF-β to the receptor to occur, the extent to which binding occurred is measured, both in the presence and in the absence of the compound to be assessed. Comparison of the two values shows whether the compound blocked TGF-β binding to the receptor. The TGF-β type III and type II receptors can also be used to identify TGF-β-like substances, to purify TGF-β and to identify TGF-β regions which are responsible for binding to the respective receptors. For example, the type III receptor can be used in an affinity-based method to identify substances which bind the receptor in a manner similar to TGF-β.

The invention will now be illustrated by the following examples, which are not intended to be limiting in any way.

EXAMPLES

Materials and methods used in Examples 1–5 are described below.

Materials

The following is a description of materials used in the work described herein.

Recombinant human TGF-β1 was provided by Rik Derynck of Genentech. COS-M6 cells were provided by Brian Seed of the Massachusetts General Hospital and Alejandro Aruffo of Bristol-Myers-Squibb. Heparitinase was provided by Tetsuhito Kojima and Robert Rosenberg of MIT. LLC-PK$_1$ cells were a gift of Dennis Ausiello of the Massachusetts General Hospital. YH-16 cell were a gift of Edward Yeh of the Massachusetts General Hospital. 3–4 cells were a gift of Eugene Kaji of the Whitehead Institute for Biomedical Research. All other cell lines were purchased from ATCC and grown as specified by the supplier, except as noted.

Expression Cloning

Construction of CDNA Library and Generation of Plasmid Pools

10 μg polyadenylated mRNA was prepared from A10 cells by the proteinase-K/SDS method (Gonda et al., *Molec. Cell. Biol.* 2: 617–624 (1982)). Double stranded cDNA was synthesized and linkered to nonpalindromic BstX1 adaptors as described by Seed, B. and A. Aruffo, *Proc. Natl. Acad. Sci. USA* 84: 3365–3369 (1987). Acaptored CDNA was size-fractionated on a 5 to 20% potassium acetate gradient, and inserts greater than 1 kb were ligated to the plasmid vector pcDNA-1, and electroporated in the *E. coli* MC1061/P3, yielding a primary library with a titer of >$10^7$ recombinants. A portion of the cDNA was plated as pools of ~$1 \times 10^4$ recombinant bacteria colonies grown on 15 cm petri dishes with Luria-broth agar containing 7.5 mg/ml tetracycline and 12.5 mg/ml ampicillin. Cells were scraped off the plates in 10 mls of Luria-broth, and glycerol stocks of pooled bacteria were stored at −70° C. The remaining bacteria was used to purify plasmid DNA using the alkaline lysis mini-prep method (Sambrook, J. et al., Molecular Cloning: A Laboratory Manual, 2d Ed. (Cold Spring Harbor, N.Y., Cold Spring Harbor Laboratory Press (1989)).

COS Cell Transfections and Binding Assay

Plasmid pools (each representing ~$1 \times 10^4$ clones) were transfected into COS-M6 (subelone of COS-7 cells) by the DEAE-dextran/chloroquine method described by Seed, B. and A. Aruffo, *Proc. Natl. Acad. Sci. USA* 84: 3365–3369 (1987). Forty-eight hours after transfection, cells were incubated with 50 $p^{125}$I-TGF-β1 (100 to 200 Ci/mmol) for 4 hours at 4° C.), autoradiographic analysis of transfected cells was performed using NT-B2 photographic emulsion (Kodak) essentially as described (Gearing, D. P. et al., *EMBO J.* 8: 3667–3676 (1989)). After development of slides, cells were air-dried and mounted with mounting media and a glass coverslip. Slides were analyzed under an Olympus 0M-T1 inverted phase-contrast microscope using a dissection trans-illuminator for darkfield illumination.

Subdivision of Positive Pool

Of 86 pools screened, one pool (#13) was identified as positive and a glycerol stock of bacteria corresponding to this pool was titered and 25 pools of 1000 clones were generated and miniprep plasmid from these pools were transfected into COS cells as described above. Several positive pools of 1000 were identified, and one was replated as 25 plates of 100 colonies. A replica was made of this positive-plate and harvested. Once a positive pool was identified, individual colonies were picked from the corresponding master plate and grown overnight in 3 ml liquid culture. A 2-dimensional grid representing the 100 clones was generated and a single clone, R3-OF, was isolated.

Cloning of R3-OFF

A 208F rat fibroblast library in lambda ZAP II (Stratagene) was screened at high stringency with clone R3-OF insert, and several clones with ~6 kb inserts were isolated, one of which is referred to as R3-OFF.

DNA Sequencing and Squence Analysis

Double-stranded DNA was sequenced by the dideoxy chain termination method using Sequenase reagents (United States Biochemicals). Comparison of the sequence to the data bases was performed using BLAST (Altschcul, S. F. et al., *J. Mol. Biol.* 215: 403–410 (1990)).

Iodination of TGF-β

TGF-β1 was iodinated using the chloramine-T method as described (Cheifetz, S. and J. L. Andres, *J. Biol. Chem.* 263: 16984–16991 (1988)).

Chemical Cross-Linking

Transfected COS cells grown on 10 cm dishes or subconfluent L6 and A-10 cells grown on 3.5 cm dishes were incubated with $^{125}$I-TGF-β1 in binding buffer (Frebs-Ringer buffered with 20 mM Hepes, pH 7.5, 5 mM mgSO$_4$, 0.5% BSA), washed 4 times with ice-cold binding buffer without BSA, and incubated for 15 minutes with binding buffer without BSA containing 60 ng/ml disuccinimidyl suberate at 4° C. under constant rotation. Crosslinking was terminated by addition of 7% sucrose in binding buffer. Cells were scraped, collected and pelleted by centrifugation, then resuspended in lysis buffer (10 mM Tris, pH 7.4, 1 mM EDTA, pH 8.0, 1% Triton-X 100, 10 μg/ml of pepstatin, 10 μg/ml leupeptin, 10 μg/ml antipain, 100 μg/m; benzamidine hydrochloride, 100 μg/ml soybean trypsin inhibitor, 50 μg/ml aprotonin, and 1 mM phenylmethylsulfonyl fluoride). Solubilized material was analyzed by 7% SDS-PAGE and subjected to autoradiographic analysis by exposure to X-AR film (Kodak) at −70° C.

Enzymatic Digestion

Digestion of solubilized TGF-b receptors with chondroitinase and heparitinase was performed as described (Cheifetz, S. and J. L. Andres, *J. Biol. Chem.* 263: 16984–16991 (1988); Segarini, P. R. and S. M. Seyedin, *J. Biol. Chem.*, 263: 8366–8370 (1988).

Generation of Stable Cell Lines

L6 myoblasts were split 1:10 into 10 cm dishes and transfected the following day by the calcium phosphate method (Chen, C. and H. Okayama, *Molec. Cell. Biol.* 7: 2745–2752 (1987)) with clones R3-OF or R3-OFF in the forward and reverse orientations in the vector pcDNA-neo (InVitrogen). Cells were subjected to selection in the presence of G418 (Geneticin, GIBCO) for several weeks until individual colonies were visible by the naked eye. These clones were isolated and amplified.

RNA Blot Analyses

Rat tissue polyadenylated MRNA was prepared by the lithium chloride/urea method (Auffrey, C. and F. Raugeon, Eur. J. Biochemistry 107: 303–313 (1980), followed by oligo-dT cellulose chromatography (Aviv and Leder, 1972). Polyadenylated mRNA from cell lines was prepared by the proteinase K/SDS method (Gonda, T. J. et al., Molec. Cell. Biol. 2: 617–624 (1982)). Samples of mRNA were resolved by electrophoresis on 1% agarose-2.2M formaldehyde gels, blotted onto nylon membranes (Biotrns, ICN) and incubated with the 2.9 kb insert of clone Re-OF labeled with $^{32}$p by random priming as probe (Sambrook, J. et al., Molecular Cloning: A Laboratory Manual, 2d Ed., Cold Spring Harbor, N.Y., Cold Spring Harbor Laboratory Press, (1989). Hybridizations were performed at 42° C. in hybridization buffer containing 50% formamide overnight, and blots were washed at 55° C. in 0.2× SSC, 0.1% SDS, before exposure to X-AR film at −70° C.

Example 1

Production of Anti-Type III Receptor Protein Antibodies and Microsequencing and Microsequencing of Peptides Resulting from Partial Proteolysis of Purified Type III Receptor Initially cellular proteoglycans were purified from human placenta and then subjected to enzymatic deglycosylation with heparitinase and chondroitinase. Protein cores in the molecular weight range of 100–130 kilodaltons were further purified by preparative gel electrophoresis; these should include the type III receptor. This partially purified material was used as an immunogen in mice. After screening 850 hybridoma lines developed from immunized mice, three lines were found to produce antibodies that specifically recognized and immunoprecipitated a deglycosylated polypeptide species of 100–120 kD. This species could be radiolabelled by incubation of whole cells with $^{125}$ I-TGF-β followed by covalent cross-linking. Its size is consistent with that of the protein core previously reported for the type III receptor. (Massague, J., Annu. Rev. Cell. Biol. 6: 597–641 (1990))

Monoclonal antibody 94 was used to purify the type III receptor from rat liver by affinity-chromatography. The purified receptor was subjected to partial proteolysis and the resulting peptides were resolved by high pressure liquid chromatography. Several peptides were subjected to microsequencing and yielded the following oligopeptide sequences:

Peptide I: ILLDPDHPPAL (SEQ ID NO: 1)
Peptide II: QAPFPINFMIA (SEQ ID NO: 2)
Peptide III: QPIVPSVQ (SEQ ID NO: 3)
Peptide IV: FYVEQGYGR (SEQ ID NO: 4)

These peptide sequences were used to construct degenerate oligonucleotides that served either as primers in a cloning strategy using the polymerase chain reaction (PCR) or as probes in screening cDNA libraries. While this strategy was not productive, the oligopeptide sequences proved useful in verifying the receptor clones isolated by the second, alternative strategy (see Example 2).

Example 2

Expression Cloning of the Type III Receptor cDNA

An expression cloning strategy in COS cells, a procedure which takes advantage of the considerable amplification of individual cDNAs in transfected COS cells was used as an alternative means to isolate TGF-β receptor clones. Such amplification is mediated by SV40 large T antigen expressed by the COS cells interacting with a SV40 origin of replication in the CDNA vector. Gearing, D. et al., EMBO J. 8: 3667–3676 (1989); Lin, H. Y., et al., Proc. Natl. Acad. Sci. 88: 3185–3189 (1991a); Lin, H. Y. et al., Science, in press (1991); Mathews, L. S. and Vale, W. W., Cell 65: 973–982 (1991).

The strategy involved the construction of a cDNA library from A-10 cells, a rat vascular smooth muscle cell line that expresses all three high-affinity TGF-β receptors. The resulting cDNAs were inserted into the vector pcDNA-1, which carries the CMV transcriptional promoter and the SV40 origin of replication. The resulting library was then divided into pools of 10,000 independent recombinants each and DNA from each pool was transfected into 1.5×10$^6$ COS-7 cells grown on glass flaskettes by means of DEAE-dextran transfection procedure. Aruffo, A. and Seed, B., Proc. Natl. Acad. Sci. U.S.A. 84: 8573–8577 (1987); Gearing, D. et al., EMBO J. 8: 3667–3676 (1989); Mathews, L. S. and Vale, W. W., Cell 65: 973–982 (1991). The transfected cells were cultured for 48–60 hours and then exposed to radiolabelled TGF-β1 for four hours. Following this treatment, the glass slides carrying these cells were washed extensively and fixed. These slides were dipped in liquid photographic emulsion and examined by darkfield microscopy. While all of the receptor genes cloned to date by this procedure have undetectable or low constitutive levels of expression in COS cells, we were hindered by the fact that untransfected COS cells already express substantial amounts of type III TGF-β receptor. Such expression, estimated to be approximately 2×10$^5$ receptor molecules per cell, might well have generated an unacceptably high level of background binding. However, since the detection procedure involves visualizing radiolabelled ligand-binding on individual cells, it was hoped that identifying occasional cells expressing substantially higher levels of vector-encoded receptor would be possible. This hope was vindicated in the initial experiments.

After screening nearly one million cDNA clones in this manner, a glass slide containing 20 positive transfectants was identified. The original pool of expression constructs from which one such transfectant was derived was split into 25 subpools of 1000 clones each and these were subjected to a second round of screening. Two further rounds of sib-selection resulted in the isolation of a cDNA clone (R3-OF) with a 2.9 kb insert that induced high levels of TGF-β-binding proteins in approximately 10% of COS cells into which it was transfected.

The specificity of this binding was validated by showing that addition of a 200-fold excess of unlabeled TGF-β competitor strongly reduced binding of $^{128}$I-TGF-β to transfected cells. By taking into account a transfection efficiency of 10% and the high background of endogenous receptor expression, we calculated that the level of total $^{128}$ I-TGF-β binding to each glass slide of cells transfected with this cDNA clone was only 2-fold above the level seen with mock transfectants (data not shown). Nonetheless, this marginal increase in ligand-binding was sufficient to identify rare transfectants amidst a large field of cells expressing this background level of receptor.

The R3-OF cDNA encoded an open reading frame of 836 amino acid residues of which the 3' most 18 were encoded by vector sequence, clearly indicating that clone R3-OF was an incomplete cDNA insert which ended prematurely at the codon specifying alanine 818 (FIG. 4). R3-OF was used as a probe to isolate a full-length cDNA from a rat 208 F lambda phage library. This clone, termed R3-OFF, was 6 kb in length and encoded a protein of 853 amino acids; its sequence was co-linear with that of clone R3-OF.

Example 3

Characterization of the Product of the Full Length Clone R3-OFF

Characterization of the product of the full length clone R3-OFF was undertaken in order to determine which of the three TGF-β receptors it specified. To do so, COS transfectants were incubated with radioiodinated TGF-β, chemical crosslinker was added and the labelled receptors were resolved by polyacrylamide gel electrophoresis.

Labelling of cell surface TGF-β receptors in this way resulted in the detection of three distinct species on the surface of COS cells, as extensively by others (Massague, J. et al., *Ann. NY Acad. Sci.* 593: 59–72 (1990). These included the two lower molecular weight type I and II receptors (65 and 85 kD) and the higher molecular weight type III proteoglycan, which migrated as a diffuse band of 280–330 kd. Enzymatic treatment of the proteoglycan with chondroitinase and heparitinase yielded a core protein of approximately 100 kd. Binding to all three receptor types was specific, in that it was completed by 200-fold excess of unlabeled TGF-β1.

Transfecting the R3-OFF cDNA caused a two-fold increase in expression of the type III receptor. When a cell lysate derived from COS cells transfected with clone R3-OFF was treated with deglycosylating enzymes, the heterogenous 280–230 kd band was converted to a protein core which co-migrated with the type III protein core seen in untransfected A10 cells. Importantly, the recombinant protein core migrates differently from the endogenous COS cell type III protein core.

These observaltions were confirmed and extended in experiments using stably transfected cells expressing the R3-OFF cDNA. L6 rat skeleton muscle myoblasts normally do not express detectable type III mRNA or endogenous type III receptor (determined by radiolabelled ligand-binding assay). Such cells were transfected with the isolated cDNA in the vector pcDNA-neo. Cell clones stably expressing this clone in both the forward and reverse orientations with respect to the CMV promoter were isolated and analyzed by ligand-binding assay.

Introductior of either the full length clone R3-OFF or the partial clone R3-OF in the forward orientation led to the de novo expression of the type III receptor. L6 cells transfected with the cDNA in reversed orientation did not express this protein. The apparent size of the protein core of the type III receptor in cells transfected with the R3-OF clone is smaller than that expressed by R3-OFF transfected cells, consistent with the difference in the sizes of the protein cores predicted from the respective nucleic acid sequences (FIGS. 1A–1C).

Unexpectedly the amount of radio-labelled ligand corsslinked to the type II receptor is increased by 2.5 fold in cells expressing the type III cDNA, while the amount crosslinked to the type I receptor remained unchanged. This apparent specific up-regulation of ligand-binding to the type II receptor could be detected with all of the 15 stably transfected L6 cell lines analyzed so far. This effect seems to be mediated by the truncated clone R3-OF which lacks the cytoplasmic domain as well as by the full-length clone R3-OFF.

Example 4

Expression of Type III Receptor

Northern blot analysis demonstrated that the type III receptor mRNA is expressed as a single 6 kb message in several rat tissues. The level of MRNA expression in the liver was less than in other tissues, a result expected from earlier surveys of various tissues using radioiodinated TGF-μ1. Based on this information, it appears that clone R3-OFF, with a ~6 kb cDNA insert, represents a full length rat type III cDNA clone.

Cells of mouse origin (MEL and YH16) appear to express a smaller (~5.5 kb) message for the type III MRNA than those of pig, rat and human origin. In all of these cells, expression or absence of the type III mRNA is consistent with the expression or absence of detectable cell surface type III receptors with the notable exception of the retinoblastoma cell lines (Y79, Weri-1, Weri-24, and Weri-27). These cells have previously been shown to lack detectable surface expression of type III receptor, a result confirmed by our own unpublished work. It is striking that the type III receptor mRNA is expressed in these cells at a level comparable to that of other cells that do indeed express type III receptor proteins at readily detectable levels. At this moment, we can only conclude that TGF-β receptor III expression, which is substantial in normal retinoblasts (AD12), has been down-regulated in these retinoblastoma tumor cells, perhaps through post-transcriptional mechanisms.

Example 5

Sequence Analysis of the Full-Length Type III cDNA

The full-length cDNA clone (R3-OFF), described in Example 4, was subjected to sequence analysis. The full reading frame along with flanking sequences is presented in FIGS. 1A–1C. This reading frame encodes a protein of 853 amino acid residues, which is compatible with the 100 kD observed for the fully deglycosylated TGF-β type III receptor.

Two segments of derived protein sequence (underlined and italicized, residues 378–388 and 427–434) precisely match those determined earlier from direct biochemical analysis of the purified receptor protein. This further secured the identity of this isolated cDNA clone as encoding the rat type III receptor.

This TGF-β binding protein has an unusual structure for a cytokine receptor. Hydropathy analysis indicates a N-terminal signal sequence, followed by a long, hydrophilic N-terminal region (Kyte, J. and R. F. Doolittle, *J. Mol. Biol.* 157: 105–132 (1982)). A 27 residue region of strong hydrophobicity (underlined, residues 786–812) toward the C-terminus represents the single putative transmembrane domain. This suggests that nearly all of the receptor is composed of an N-terminal extracellular domain that is anchored to the plasma membrane near its C-terminus. A relatively short C-terminal tail of 41 residues represents the putative cytoplasmic domain.

The clone R3-OF was also analyzed and found to be a truncated version of R3-OFF, with an identical open reading frame but whose last encoded residue is alanine 818 (FIGS. 1A–1C).

In R3-OFF there are six consensus N-linked glycosylation sites and 15 cysteines (indicated in FIGS. 1A–1C). There, is at least one consensus glycosaminoglycan addition site at serine 535 (Bernfield, M. and K. C. Hooper, *Ann. N.Y. Acad. Sci.* in press (1991), and numerous Ser-Gly residues that are potential sites for GAG conjugation. A consensus protein kinase C site is also present at residue 817.

Only one other gene described to date, a glycoprotein expressed in high quantities by endothelial cells and termed endoglin (Gougos and Letarte, 1990), contains a related amino acid sequence. Overall, there is ~30% identity with the type III receptor over the entire 645 amino acid residue length of endoglin. The most homologous regions between the sequences of the type III receptor and endoglin (74% identity) falls primarily in the putative transmembrane and cytoplasmic domains. Similar to the general structure of type III receptor, endoglin is a glycoprotein which contains a large hydrophilic and presumably extracellular N-terminal domain followed by a putative transmembrane domain and a short cytoplasmic tail of 47 amino acid residues. The biological role of endoglin is unclear, though it has been suggested that it may involve cell-cell recognition through interactions of an "RGD" sequence on its ectodomain with other adhesion molecules. Unlike the TGF-β type III receptor, endoglin does not carry GAG groups.

Equivalents

Those skilled in the art will recognize, or be able to ascertain using not more than routine experimentation, many equivalents to the specific embodiments of the invention described herein. Such equivalents are intended to be encompassed by the following claims.

We claim:

1. A method of altering TGF-β binding to TGF-β type II receptor on the surface of a cell, comprising combining with the cell a preparation consisting essentially of a soluble polypeptide comprising the amino acid sequence of the extracellular domain of a mammalian TGF-β type II receptor protein, wherein the amino acid sequence of the mammalian receptor protein is:

(a) the amino acid sequence of the TGF-β type II receptor protein of SEQ ID NO: 8, or (b) the amino acid sequence of a TGF-β type II receptor protein encoded by mammalian DNA which hybridizes to a probe having the sequence of the complement of SEQ ID NO: 7 under high stringency conditions;

wherein the polypeptide and cell are combined under conditions appropriate for binding of the soluble TGF-β type II receptor to TGF-β.

2. A method according to claim 1, wherein the mammalian TGF-β type II receptor protein has the amino acid sequence set forth in SEQ ID NO: 8.

3. The method of claim 1, wherein TGF-β binding is inhibited.

4. A method of altering TGF-β binding to TGF-β type II receptor on the surface of a cell, comprising combining with the cell a preparation consisting essentially of a soluble polypeptide comprising the amino acid sequence of the extracellular domain of a mammalian TGF-β type II receptor protein, wherein the mammalian receptor protein has the amino acid sequence encoded by:

(a) the cDNA insert contained in the plasmid deposited under ATCC accession number 209455, or (b) a cDNA molecule which is present in a mammalian library and which hybridizes with a probe having the sequence of the complement of the coding sequence of the cDNA insert contained in the plasmid deposited under ATCC accession number 209455 under stringency conditions sufficient to specifically identify the cDNA molecule in the library;

wherein the polypeptide and cell are combined under conditions appropriate for binding of the soluble TGF-β type II receptor to TGF-β.

5. A method according to claim 4, wherein the mammalian TGF-β type II receptor protein has the amino acid sequence encoded by the cDNA insert contained in the plasmid deposited under ATCC accession number 209455.

6. A method of altering TGF-β binding to TGF-β type II receptor on the surface of a cell, comprising combining with the cell a preparation consisting essentially of a polypeptide comprising part of the amino acid sequence of a mammalian TGF-β type II receptor protein, wherein the mammalian receptor protein has the amino acid sequence of:

(a) the amino acid sequence of the TGF-β type II receptor protein of SEQ ID NO: 8, or (b) the amino acid sequence encoded by mammalian DNA which hybridizes to a probe having the sequence of the complement of SEQ ID NO: 7 under high stringency conditions;

wherein the amino acid sequence of the polypeptide comprises a contiguous fragment of the mature mammalian type II receptor sequence which includes the TGF-β-binding site;

wherein the polypeptide specifically binds to TGF-β;

and wherein the polypeptide and cell are combined under conditions appropriate for binding of the soluble TGF-β type II receptor to TGF-β.

7. A method according to claim 6, wherein the mammalian TGF-β type II receptor protein has the amino acid sequence set forth in SEQ ID NO: 8.

8. A method according to claim 6, wherein the polypeptide comprises the amino acid sequence of the extracellular domain of the TGF-β type II receptor protein having the sequence of SEQ ID NO: 8.

9. A method of altering TGF-β binding to TGF-β type II receptor on the surface of a cell, comprising combining with the cell a preparation consisting essentially of a polypeptide comprising part of the amino acid sequence of a mammalian TGF-β type II receptor protein, wherein the mammalian receptor protein has the amino acid sequence encoded by:

(a) the cDNA insert contained in the plasmid deposited under ATCC accession number 209455, or (b) a cDNA molecule which is present in a mammalian library and which hybridizes with a probe having the sequence of the complement of the coding sequence of the cDNA insert contained in the plasmid deposited under ATCC accession number 209455 under stringency conditions sufficient to specifically identify the cDNA molecule in the library;

wherein the amino acid sequence of the polypeptide comprises a contiguous fragment of the mature mammalian type II receptor sequence which includes the TGF-β-binding site;

wherein the polypeptide specifically binds to TGF-β;

and wherein the polypeptide and cell are combined under conditions appropriate for binding of the soluble TGF-β type II receptor to TGF-β.

10. A method according to claim 9, wherein the mammalian TGF-β type II receptor protein has the amino acid sequence encoded by the cDNA insert contained in the plasmid deposited under ATCC accession number 209455.

11. A method according to claim 9, wherein the polypeptide comprises the amino acid sequence of the extracellular domain of the TGF-β type II receptor protein encoded by the cDNA insert contained in the plasmid deposited under ATCC accession number 209455.

12. A method of modulating the effects of TGF-β in a mammal, comprising administering to the mammal a polypeptide comprising the amino acid sequence of a mammalian TGF-β type II receptor wherein the mammalian receptor has the amino acid sequence of:

a) the amino acid sequence of the TGF-β type II receptor protein of SEQ ID NO: 8, or b) the amino acid sequence encoded by mammalian DNA which hybridizes under high stringency conditions to a probe having the sequence of the complement of SEQ ID NO: 7;

wherein the polypeptide is administered to the mammal in sufficient quantity to alter binding of TGF-β to endogenous TGF-β type II receptors, type III receptors, or both.

13. A method according to claim 12, wherein the mammalian TGF-β type II receptor protein has the amino acid sequence set forth in SEQ ID NO: 8.

14. A method of modulating the effects of TGF-β in a mammal, comprising administering to the mammal a polypeptide comprising the amino acid sequence of a mammalian TGF-β type II receptor wherein the mammalian receptor protein has the amino acid sequence encoded by:

a) the cDNA insert contained in the plasmid deposited under ATCC accession number 209455, or b) a cDNA molecule which is present in a mammalian library and which hybridizes with a probe having the sequence of the complement of the coding sequence of the cDNA insert contained in the plasmid deposited under ATCC accession number 209455 under stringency conditions sufficient to specifically identify the cDNA molecule in the library;

wherein the polypeptide is administered to the mammal in sufficient quantity to alter binding of TGF-β to endogenous TGF-β type II receptors, type III receptors, or both.

15. A method according to claim 14, wherein the mammalian TGF-β type II receptor protein has the amino acid sequence encoded by the cDNA insert contained in the plasmid deposited under ATCC accession number 209455.

16. A method of modulating the effects of TGF-β in a mammal, comprising administering to the mammal a polypeptide comprising part of the amino acid sequence of a mammalian TGF-β type II receptor protein, wherein the mammalian receptor protein has the amino acid sequence of:

a) the amino acid sequence of the TGF-β type II receptor protein of SEQ ID NO: 8, or b) the amino acid sequence encoded by mammalian DNA which hybridizes to a probe having the sequence of the complement of SEQ ID NO: 7 under high stringency conditions;

wherein the amino acid sequence of the polypeptide comprises a contiguous fragment of the mature mammalian type II receptor sequence which includes the TGF-β-binding site;

wherein the polypeptide specifically binds to TGF-β under conditions appropriate for binding of the TGF-β type II receptor to TGF-β;

and wherein the polypeptide is administered to the mammal in sufficient quantity to alter binding of TGF-β to endogenous TGF-β type II receptors, type III receptors, or both.

17. A method according to claim 16, wherein the mammalian TGF-β type II receptor protein has the amino acid sequence set forth in SEQ ID NO: 8.

18. A method according to claim 16, wherein the polypeptide comprises the amino acid sequence of the extracellular domain of the TGF-β type II receptor protein having the sequence of SEQ ID NO: 8.

19. A method of modulating the effects of TGF-β in a mammal comprising administering to the mammal a polypeptide comprising part of the amino acid sequence of a mammalian TGF-β type II receptor protein, wherein the mammalian receptor protein has the amino acid sequence encoded by;

a) the cDNA insert contained in the plasmid deposited under ATCC accession number 209455, or b) a cDNA molecule which is present in a mammalian library and which hybridizes with a probe having the sequence of the complement of the coding sequence of the cDNA insert contained in the plasmid deposited under ATCC accession number 209455 under stringency conditions sufficient to specifically identify the cDNA molecule in the library;

wherein the amino acid sequence of the polypeptide comprises a contiguous fragment of the mature mammalian type II receptor sequence which includes the TGF-β-binding site;

wherein the polypeptide specifically binds to TGF-β under conditions appropriate for binding of the soluble TGF-β type II receptor to TGF-β;

and wherein the polypeptide is administered to the mammal in sufficient quantity to alter binding of TGF-β to endogenous TGF-β type II receptors, type III receptors, or both.

20. A method according to claim 19, wherein the mammalian TGF-β type II receptor protein has the amino acid sequence encoded by the cDNA insert contained in the plasmid deposited under ATCC accession number 209455.

21. A method according to claim 19, wherein the polypeptide comprises the amino acid sequence of the extracellular domain of the TGF-β type II receptor protein encoded by the cDNA insert contained in the plasmid deposited under ATCC accession number 209455.

* * * * *

```
                          SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
         (A) LENGTH: 11 amino acids
         (B) TYPE: amino acid
         (C) STRANDEDNESS: double
         (D) TOPOLOGY: linear (xi) SEQUENCE DESCRIPTION: SEQ ID NO:1:

Ile Leu Leu Asp Pro Asp His Pro Pro Ala Leu
1               5                   10

(2) INFORMATION FOR SEQ ID NO:2:

(i) SEQUENCE CHARACTERISTICS:
         (A) LENGTH: 11 amino acids
         (B) TYPE: amino acid
         (C) STRANDEDNESS: double
         (D) TOPOLOGY: linear (xi) SEQUENCE DESCRIPTION: SEQ ID NO:2:

Gln Ala Pro Phe Pro Ile Asn Phe Met Ile Ala
1               5                   10

(2) INFORMATION FOR SEQ ID NO:3:

(i) SEQUENCE CHARACTERISTICS:
         (A) LENGTH: 8 amino acids
         (B) TYPE: amino acid
         (C) STRANDEDNESS: double
         (D) TOPOLOGY: linear (xi) SEQUENCE DESCRIPTION: SEQ ID NO:3:

Gln Pro Ile Val Pro Ser Val Gln
1               5

(2) INFORMATION FOR SEQ ID NO:4:

(i) SEQUENCE CHARACTERISTICS:
         (A) LENGTH: 9 amino acids
         (B) TYPE: amino acid
         (C) STRANDEDNESS: double
         (D) TOPOLOGY: linear (xi) SEQUENCE DESCRIPTION: SEQ ID NO:4:

Phe Tyr Val Glu Gln Gly Tyr Gly Arg
1               5
```

-continued (2) INFORMATION FOR SEQ ID NO:5:

(i) SEQUENCE CHARACTERISTICS:
  (A) LENGTH: 3237 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: CDS
  (B) LOCATION: 241..2799

(xi) SEQUENCE DESCRIPTION: SEQ ID NO:5:

```
CAGGAGGTGA AAGTCCCCGG CGGTCCGGAT GGCGCAGTTG CACTGCGCTG CTGAGCTCGC      60

GGCCGCCTGC GCACACTGGG GGGACTCGCT TCGGCTAGTA ACTCCTCCAC CTCGCGGCGG     120

ACGACCGGTC CTGGACACGC TGCCTGCGAG GCAAGTTGAA CAGTGCAGAG AAGGATCTTA     180

AAGCTACACC CGACTTGCCA CGATTGCCTT CAATCTGAAG AACCAAAGGC TGTTGGAGAG     240

ATG GCA GTG ACA TCC CAC CAC ATG ATC CCG GTG ATG GTT GTC CTG ATG      288
Met Ala Val Thr Ser His His Met Ile Pro Val Met Val Val Leu Met
 1               5                  10                  15

AGC GCC TGC CTG GCC ACC GCC GGT CCA GAG CCC AGC ACC CGG TGT GAA      336
Ser Ala Cys Leu Ala Thr Ala Gly Pro Glu Pro Ser Thr Arg Cys Glu
            20                  25                  30

CTG TCA CCA ATC AAC GCC TCT CAC CCA GTC CAG GCC TTG ATG GAG AGC      384
Leu Ser Pro Ile Asn Ala Ser His Pro Val Gln Ala Leu Met Glu Ser
        35                  40                  45

TTC ACC GTT CTG TCT GGC TGT GCC AGC AGA GGC ACC ACC GGG CTG CCA      432
Phe Thr Val Leu Ser Gly Cys Ala Ser Arg Gly Thr Thr Gly Leu Pro
    50                  55                  60

AGG GAG GTC CAT GTC CTA AAC CTC CGA AGT ACA GAT CAG GGA CCA GGC      480
Arg Glu Val His Val Leu Asn Leu Arg Ser Thr Asp Gln Gly Pro Gly
 65                  70                  75                  80

CAG CGG CAG AGA GAG GTT ACC CTG CAC CTG AAC CCC ATT GCC TCG GTG      528
Gln Arg Gln Arg Glu Val Thr Leu His Leu Asn Pro Ile Ala Ser Val
                85                  90                  95

CAC ACT CAC CAC AAA CCT ATC GTG TTC CTG CTC AAC TCC CCC CAG CCC      576
His Thr His His Lys Pro Ile Val Phe Leu Leu Asn Ser Pro Gln Pro
            100                 105                 110

CTG GTG TGG CAT CTG AAG ACG GAG AGA CTG GCC GCT GGT GTC CCC AGA      624
Leu Val Trp His Leu Lys Thr Glu Arg Leu Ala Ala Gly Val Pro Arg
        115                 120                 125

CTC TTC CTG GTT TCG GAG GGT TCT GTG GTC CAG TTT CCA TCA GGA AAC      672
Leu Phe Leu Val Ser Glu Gly Ser Val Val Gln Phe Pro Ser Gly Asn
    130                 135                 140

TTC TCC TTG ACA GCA GAA ACA GAG GAA AGG AAT TTC CCT CAA GAA AAT      720
Phe Ser Leu Thr Ala Glu Thr Glu Glu Arg Asn Phe Pro Gln Glu Asn
145                 150                 155                 160

GAA CAT CTC GTG CGC TGG GCC CAA AAG GAA TAT GGA GCA GTG ACT TCG      768
Glu His Leu Val Arg Trp Ala Gln Lys Glu Tyr Gly Ala Val Thr Ser
                165                 170                 175

TTC ACT GAA CTC AAG ATA GCA AGA AAC ATC TAT ATT AAA GTG GGA GAA      816
Phe Thr Glu Leu Lys Ile Ala Arg Asn Ile Tyr Ile Lys Val Gly Glu
            180                 185                 190

GAT CAA GTG TTT CCT CCT ACG TGT AAC ATA GGG AAG AAT TTC CTC TCA      864
Asp Gln Val Phe Pro Pro Thr Cys Asn Ile Gly Lys Asn Phe Leu Ser
        195                 200                 205

CTC AAT TAC CTT GCC GAG TAC CTT CAA CCC AAA GCC GCC GAA GGT TGT      912
Leu Asn Tyr Leu Ala Glu Tyr Leu Gln Pro Lys Ala Ala Glu Gly Cys
```

```
                210                     215                     220
GTC CTG CCC AGT CAG CCC CAT GAA AAG GAA GTA CAC ATC ATC GAG TTA    960
Val Leu Pro Ser Gln Pro His Glu Lys Glu Val His Ile Ile Glu Leu
225             230                 235                     240

ATT ACC CCC AGC TCG AAC CCT TAC AGC GCT TTC CAG GTG GAT ATA ATA   1008
Ile Thr Pro Ser Ser Asn Pro Tyr Ser Ala Phe Gln Val Asp Ile Ile
                245                 250                 255

GTT GAC ATA CGA CCT GCT CAA GAG GAT CCC GAG GTG GTC AAA AAC CTT   1056
Val Asp Ile Arg Pro Ala Gln Glu Asp Pro Glu Val Val Lys Asn Leu
                260                 265                 270

GTC CTG ATC TTG AAG TGC AAA AAG TCT GTC AAC TGG GTG ATC AAG TCT   1104
Val Leu Ile Leu Lys Cys Lys Lys Ser Val Asn Trp Val Ile Lys Ser
                275                 280                 285

TTT GAC GTC AAG GGA AAC TTG AAA GTC ATT GCT CCC AAC AGT ATC GGC   1152
Phe Asp Val Lys Gly Asn Leu Lys Val Ile Ala Pro Asn Ser Ile Gly
            290                 295                 300

TTT GGA AAA GAG AGT GAA CGA TCC ATG ACA ATG ACC AAA TTG GTA AGA   1200
Phe Gly Lys Glu Ser Glu Arg Ser Met Thr Met Thr Lys Leu Val Arg
305                 310                 315                 320

GAT GAC ATC CCT TCC ACC CAA GAG AAT CTG ATG AAG TGG GCA CTG GAC   1248
Asp Asp Ile Pro Ser Thr Gln Glu Asn Leu Met Lys Trp Ala Leu Asp
                325                 330                 335

AAT GGC TAC AGG CCA GTG ACG TCA TAC ACA ATG GCT CCC GTG GCT AAT   1296
Asn Gly Tyr Arg Pro Val Thr Ser Tyr Thr Met Ala Pro Val Ala Asn
                340                 345                 350

AGA TTT CAT CTT CGG CTT GAG AAC AAC GAG GAG ATG AGA GAT GAG GAA   1344
Arg Phe His Leu Arg Leu Glu Asn Asn Glu Glu Met Arg Asp Glu Glu
                355                 360                 365

GTC CAC ACC ATT CCT CCT GAG CTT CGT ATC CTG CTG GAC CCT GAC CAC   1392
Val His Thr Ile Pro Pro Glu Leu Arg Ile Leu Leu Asp Pro Asp His
370                 375                 380

CCG CCC GCC CTG GAC AAC CCA CTC TTC CCA GGA GAG GGA AGC CCA AAT   1440
Pro Pro Ala Leu Asp Asn Pro Leu Phe Pro Gly Glu Gly Ser Pro Asn
385                 390                 395                 400

GGT GGT CTC CCC TTT CCA TTC CCG GAT ATC CCC AGG AGA GGC TGG AAG   1488
Gly Gly Leu Pro Phe Pro Phe Pro Asp Ile Pro Arg Arg Gly Trp Lys
                405                 410                 415

GAG GGC GAA GAT AGG ATC CCC CGG CCA AAG CAG CCC ATC GTT CCC AGT   1536
Glu Gly Glu Asp Arg Ile Pro Arg Pro Lys Gln Pro Ile Val Pro Ser
                420                 425                 430

GTT CAA CTG CTT CCT GAC CAC CGA GAA CCA GAA GAA GTG CAA GGG GGC   1584
Val Gln Leu Leu Pro Asp His Arg Glu Pro Glu Glu Val Gln Gly Gly
                435                 440                 445

GTG GAC ATC GCC CTG TCA GTC AAA TGT GAC CAT GAA AAG ATG GTC GTG   1632
Val Asp Ile Ala Leu Ser Val Lys Cys Asp His Glu Lys Met Val Val
450                 455                 460

GCT GTA GAC AAA GAC TCT TTC CAG ACC AAT GGC TAC TCA GGG ATG GAG   1680
Ala Val Asp Lys Asp Ser Phe Gln Thr Asn Gly Tyr Ser Gly Met Glu
465                 470                 475                 480

CTC ACC CTG TTG GAT CCT TCG TGT AAA GCC AAA ATG AAT GGT ACT CAC   1728
Leu Thr Leu Leu Asp Pro Ser Cys Lys Ala Lys Met Asn Gly Thr His
                485                 490                 495

TTT GTT CTC GAG TCT CCC CTG AAT GGC TGT GGT ACT CGA CAT CGG AGG   1776
Phe Val Leu Glu Ser Pro Leu Asn Gly Cys Gly Thr Arg His Arg Arg
                500                 505                 510

TCG ACC CCG GAT GGT GTG GTT TAC TAT AAC TCT ATT GTG GTG CAG GCT   1824
Ser Thr Pro Asp Gly Val Val Tyr Tyr Asn Ser Ile Val Val Gln Ala
                515                 520                 525

CCG TCC CCT GGG GAT AGC AGT GGC TGG CCT GAT GGC TAT GAA GAC TTG   1872
```

-continued

| | | |
|---|---|---|
| Pro Ser Pro Gly Asp Ser Ser Gly Trp Pro Asp Gly Tyr Glu Asp Leu<br>530 535 540 | | |
| GAG TCA GGC GAT AAT GGA TTT CCT GGA GAC GGG GAT GAA GGA GAA ACT<br>Glu Ser Gly Asp Asn Gly Phe Pro Gly Asp Gly Asp Glu Gly Glu Thr<br>545 550 555 560 | 1920 | |
| GCC CCC CTG AGC CGA GCT GGA GTG GTG GTG TTT AAC TGC AGC TTG CGG<br>Ala Pro Leu Ser Arg Ala Gly Val Val Val Phe Asn Cys Ser Leu Arg<br>565 570 575 | 1968 | |
| CAG CTG AGG AAT CCC AGT GGC TTC CAG GGC CAG CTC GAT GGA AAT GCT<br>Gln Leu Arg Asn Pro Ser Gly Phe Gln Gly Gln Leu Asp Gly Asn Ala<br>580 585 590 | 2016 | |
| ACC TTC AAC ATG GAG CTG TAT AAC ACA GAC CTC TTT CTG GTG CCC TCC<br>Thr Phe Asn Met Glu Leu Tyr Asn Thr Asp Leu Phe Leu Val Pro Ser<br>595 600 605 | 2064 | |
| CCA GGG GTC TTC TCT GTG GCA GAG AAC GAG CAT GTT TAT GTT GAG GTG<br>Pro Gly Val Phe Ser Val Ala Glu Asn Glu His Val Tyr Val Glu Val<br>610 615 620 | 2112 | |
| TCT GTC ACC AAG GCT GAC CAA GAT CTG GGA TTC GCC ATC CAA ACC TGC<br>Ser Val Thr Lys Ala Asp Gln Asp Leu Gly Phe Ala Ile Gln Thr Cys<br>625 630 635 640 | 2160 | |
| TTT CTC TCT CCA TAC TCC AAC CCA GAC AGA ATG TCT GAT TAC ACC ATC<br>Phe Leu Ser Pro Tyr Ser Asn Pro Asp Arg Met Ser Asp Tyr Thr Ile<br>645 650 655 | 2208 | |
| ATC GAG AAC ATC TGT CCG AAA GAC GAC TCT GTG AAG TTC TAC AGC TCC<br>Ile Glu Asn Ile Cys Pro Lys Asp Asp Ser Val Lys Phe Tyr Ser Ser<br>660 665 670 | 2256 | |
| AAG AGA GTG CAC TTT CCC ATC CCG CAT GCT GAG GTG GAC AAG AAG CGC<br>Lys Arg Val His Phe Pro Ile Pro His Ala Glu Val Asp Lys Lys Arg<br>675 680 685 | 2304 | |
| TTC AGC TTC CTG TTC AAG TCT GTG TTC AAC ACC TCC CTG CTC TTC CTG<br>Phe Ser Phe Leu Phe Lys Ser Val Phe Asn Thr Ser Leu Leu Phe Leu<br>690 695 700 | 2352 | |
| CAC TGC GAG TTG ACT CTG TGC TCC AGG AAG AAG GGC TCC CTG AAG CTG<br>His Cys Glu Leu Thr Leu Cys Ser Arg Lys Lys Gly Ser Leu Lys Leu<br>705 710 715 720 | 2400 | |
| CCG AGG TGT GTG ACT CCT GAC GAC GCC TGC ACT TCT CTC GAT GCC ACC<br>Pro Arg Cys Val Thr Pro Asp Asp Ala Cys Thr Ser Leu Asp Ala Thr<br>725 730 735 | 2448 | |
| ATG ATC TGG ACC ATG ATG CAG AAT AAG AAG ACA TTC ACC AAG CCC CTG<br>Met Ile Trp Thr Met Met Gln Asn Lys Lys Thr Phe Thr Lys Pro Leu<br>740 745 750 | 2496 | |
| GCT GTG GTC CTC CAG GTA GAC TAT AAA GAA AAT GTT CCC AGC ACT AAG<br>Ala Val Val Leu Gln Val Asp Tyr Lys Glu Asn Val Pro Ser Thr Lys<br>755 760 765 | 2544 | |
| GAT TCC AGT CCA ATT CCT CCT CCT CCT CCA CAG ATT TTC CAT GGC CTG<br>Asp Ser Ser Pro Ile Pro Pro Pro Pro Pro Gln Ile Phe His Gly Leu<br>770 775 780 | 2592 | |
| GAC ACG CTC ACC GTG ATG GGC ATT GCA TTT GCA GCA TTT GTG ATC GGA<br>Asp Thr Leu Thr Val Met Gly Ile Ala Phe Ala Ala Phe Val Ile Gly<br>785 790 795 800 | 2640 | |
| GCG CTC CTG ACG GGG GCC TTG TGG TAC ATC TAC TCC CAC ACA GGG GAG<br>Ala Leu Leu Thr Gly Ala Leu Trp Tyr Ile Tyr Ser His Thr Gly Glu<br>805 810 815 | 2688 | |
| ACA GCA CGA AGG CAG CAA GTC CCT ACC TCG CCG CCA GCC TCG GAG AAC<br>Thr Ala Arg Arg Gln Gln Val Pro Thr Ser Pro Pro Ala Ser Glu Asn<br>820 825 830 | 2736 | |
| AGC AGC GCG GCC CAC AGC ATC GGC AGC ACT CAG AGT ACC CCC TGC TCT<br>Ser Ser Ala Ala His Ser Ile Gly Ser Thr Gln Ser Thr Pro Cys Ser<br>835 840 845 | 2784 | |

-continued

```
AGC AGC AGC ACA GCC TAGGTGGACA GACAGACGCC CGCCCACCGC AGCCAGGGCA         2839
Ser Ser Ser Thr Ala
    850

GGGCCCGATG CCAGTGCTGC GTGTCCACAG TCAGAAGTCT TGATCTGGGC TCCCTGTAAA         2899

GAAAGAGTGA ATTTCAGTAT ACAGACAGCC AGTTCTACCC ACCCCTTACC ACGGCCCACA         2959

TAAATGTGAC CCTGGGCATC TGTCACACGA AGCTAAGCT GGTGGCCTTC CCCACCAGCC          3019

CCTCGCAGGA TGGGGGTTTC AATGTGAAAC ATCTGCCAGT TTTGTTTTGT TTTTTTAATG         3079

CTGCTTTGTC CAGGTGTCCA AACATCCATC ATTTGGGGTG GTCTGTTTTA CAGAGTAAAG         3139

GAGGCGGTGA AGGGACGTCA GCTAGTGTGT AGAGCCAAGG GGAGACAGCT AGGATTCTCG         3199

CCTAGCTGAA CCAAGGTGTA AAATAGAAGA CACGCTCC                                3237
```

(2) INFORMATION FOR SEQ ID NO:6:

(i) SEQUENCE CHARACTERISTICS:
        (A) LENGTH: 853 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Val Thr Ser His His Met Ile Pro Val Met Val Leu Met
 1               5                  10                  15

Ser Ala Cys Leu Ala Thr Ala Gly Pro Glu Pro Ser Thr Arg Cys Glu
                20                  25                  30

Leu Ser Pro Ile Asn Ala Ser His Pro Val Gln Ala Leu Met Glu Ser
            35                  40                  45

Phe Thr Val Leu Ser Gly Cys Ala Ser Arg Gly Thr Thr Gly Leu Pro
    50                  55                  60

Arg Glu Val His Val Leu Asn Leu Arg Ser Thr Asp Gln Gly Pro Gly
 65                  70                  75                  80

Gln Arg Gln Arg Glu Val Thr Leu His Leu Asn Pro Ile Ala Ser Val
                85                  90                  95

His Thr His His Lys Pro Ile Val Phe Leu Leu Asn Ser Pro Gln Pro
            100                 105                 110

Leu Val Trp His Leu Lys Thr Glu Arg Leu Ala Ala Gly Val Pro Arg
        115                 120                 125

Leu Phe Leu Val Ser Glu Gly Ser Val Val Gln Phe Pro Ser Gly Asn
    130                 135                 140

Phe Ser Leu Thr Ala Glu Thr Glu Glu Arg Asn Phe Pro Gln Glu Asn
145                 150                 155                 160

Glu His Leu Val Arg Trp Ala Gln Lys Glu Tyr Gly Ala Val Thr Ser
                165                 170                 175

Phe Thr Glu Leu Lys Ile Ala Arg Asn Ile Tyr Ile Lys Val Gly Glu
            180                 185                 190

Asp Gln Val Phe Pro Pro Thr Cys Asn Ile Gly Lys Asn Phe Leu Ser
        195                 200                 205

Leu Asn Tyr Leu Ala Glu Tyr Leu Gln Pro Lys Ala Ala Glu Gly Cys
    210                 215                 220

Val Leu Pro Ser Gln Pro His Glu Lys Glu Val His Ile Ile Glu Leu
225                 230                 235                 240

Ile Thr Pro Ser Ser Asn Pro Tyr Ser Ala Phe Gln Val Asp Ile Ile
                245                 250                 255

Val Asp Ile Arg Pro Ala Gln Glu Asp Pro Glu Val Val Lys Asn Leu
```

-continued

```
              260                 265                 270
Val Leu Ile Leu Lys Cys Lys Lys Ser Val Asn Trp Val Ile Lys Ser
            275                 280                 285

Phe Asp Val Lys Gly Asn Leu Lys Val Ile Ala Pro Asn Ser Ile Gly
290                 295                 300

Phe Gly Lys Glu Ser Glu Arg Ser Met Thr Met Thr Lys Leu Val Arg
305                 310                 315                 320

Asp Asp Ile Pro Ser Thr Gln Glu Asn Leu Met Lys Trp Ala Leu Asp
                325                 330                 335

Asn Gly Tyr Arg Pro Val Thr Ser Tyr Thr Met Ala Pro Val Ala Asn
            340                 345                 350

Arg Phe His Leu Arg Leu Glu Asn Asn Glu Glu Met Arg Asp Glu Glu
        355                 360                 365

Val His Thr Ile Pro Pro Glu Leu Arg Ile Leu Leu Asp Pro Asp His
    370                 375                 380

Pro Pro Ala Leu Asp Asn Pro Leu Phe Pro Gly Glu Gly Ser Pro Asn
385                 390                 395                 400

Gly Gly Leu Pro Phe Pro Phe Pro Asp Ile Pro Arg Arg Gly Trp Lys
                405                 410                 415

Glu Gly Glu Asp Arg Ile Pro Arg Pro Lys Gln Pro Ile Val Pro Ser
            420                 425                 430

Val Gln Leu Leu Pro Asp His Arg Glu Pro Glu Glu Val Gln Gly Gly
        435                 440                 445

Val Asp Ile Ala Leu Ser Val Lys Cys Asp His Glu Lys Met Val Val
    450                 455                 460

Ala Val Asp Lys Asp Ser Phe Gln Thr Asn Gly Tyr Ser Gly Met Glu
465                 470                 475                 480

Leu Thr Leu Leu Asp Pro Ser Cys Lys Ala Lys Met Asn Gly Thr His
                485                 490                 495

Phe Val Leu Glu Ser Pro Leu Asn Gly Cys Gly Thr Arg His Arg Arg
            500                 505                 510

Ser Thr Pro Asp Gly Val Val Tyr Tyr Asn Ser Ile Val Val Gln Ala
        515                 520                 525

Pro Ser Pro Gly Asp Ser Ser Gly Trp Pro Asp Gly Tyr Glu Asp Leu
    530                 535                 540

Glu Ser Gly Asp Asn Gly Phe Pro Gly Asp Gly Asp Glu Gly Glu Thr
545                 550                 555                 560

Ala Pro Leu Ser Arg Ala Gly Val Val Phe Asn Cys Ser Leu Arg
                565                 570                 575

Gln Leu Arg Asn Pro Ser Gly Phe Gln Gly Gln Leu Asp Gly Asn Ala
            580                 585                 590

Thr Phe Asn Met Glu Leu Tyr Asn Thr Asp Leu Phe Leu Val Pro Ser
        595                 600                 605

Pro Gly Val Phe Ser Val Ala Glu Asn Glu His Val Tyr Val Glu Val
    610                 615                 620

Ser Val Thr Lys Ala Asp Gln Asp Leu Gly Phe Ala Ile Gln Thr Cys
625                 630                 635                 640

Phe Leu Ser Pro Tyr Ser Asn Pro Asp Arg Met Ser Asp Tyr Thr Ile
                645                 650                 655

Ile Glu Asn Ile Cys Pro Lys Asp Asp Ser Val Lys Phe Tyr Ser Ser
            660                 665                 670

Lys Arg Val His Phe Pro Ile Pro His Ala Glu Val Asp Lys Lys Arg
        675                 680                 685
```

```
Phe Ser Phe Leu Phe Lys Ser Val Phe Asn Thr Ser Leu Leu Phe Leu
        690                 695                 700

His Cys Glu Leu Thr Leu Cys Ser Arg Lys Lys Gly Ser Leu Lys Leu
705                 710                 715                 720

Pro Arg Cys Val Thr Pro Asp Asp Ala Cys Thr Ser Leu Asp Ala Thr
                725                 730                 735

Met Ile Trp Thr Met Met Gln Asn Lys Lys Thr Phe Thr Lys Pro Leu
                740                 745                 750

Ala Val Val Leu Gln Val Asp Tyr Lys Glu Asn Val Pro Ser Thr Lys
                755                 760                 765

Asp Ser Ser Pro Ile Pro Pro Pro Pro Gln Ile Phe His Gly Leu
770                 775                 780

Asp Thr Leu Thr Val Met Gly Ile Ala Phe Ala Phe Val Ile Gly
785                 790                 795                 800

Ala Leu Leu Thr Gly Ala Leu Trp Tyr Ile Tyr Ser His Thr Gly Glu
                805                 810                 815

Thr Ala Arg Arg Gln Gln Val Pro Thr Ser Pro Pro Ala Ser Glu Asn
                820                 825                 830

Ser Ser Ala Ala His Ser Ile Gly Ser Thr Gln Ser Thr Pro Cys Ser
        835                 840                 845

Ser Ser Ser Thr Ala
    850
```

(2) INFORMATION FOR SEQ ID NO:7:

(i) SEQUENCE CHARACTERISTICS:
        (A) LENGTH: 2090 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 336..2038

(xi) SEQUENCE DESCRIPTION: SEQ ID NO:7:

```
GTTGGCGAGG AGTTTCCTGT TTCCCCCGCA GCGCTGAGTT GAAGTTGAGT GAGTCACTCG      60

CGCGCACGGA GCGACGACAC CCCCGCGCGT GCACCCGCTC GGGACAGGAG CCGGACTCCT     120

GTGCAGCTTC CCTCGGCCGC CGGGGGCCTC CCCGCGCCTC GCCGGCCTCC AGGCCCCTCC     180

TGGCTGGCGA GCGGGCGCCA CATCTGGCCC GCACATCTGC GCTGCCGGCC CGGCGCGGGG     240

TCCGGAGAGG GCGCGGCGCG GAGCGCAGCC AGGGGTCCGG GAAGGCGCCG TCCGTGCGCT     300

GGGGGCTCGG TCTATGACGA GCAGCGGGGT CTGCC ATG GGT CGG GGG CTG CTC       353
                                       Met Gly Arg Gly Leu Leu
                                         1               5

AGG GGC CTG TGG CCG CTG CAC ATC GTC CTG TGG ACG CGT ATC GCC AGC       401
Arg Gly Leu Trp Pro Leu His Ile Val Leu Trp Thr Arg Ile Ala Ser
                10                  15                  20

ACG ATC CCA CCG CAC GTT CAG AAG TCG GTT AAT AAC GAC ATG ATA GTC       449
Thr Ile Pro Pro His Val Gln Lys Ser Val Asn Asn Asp Met Ile Val
        25                  30                  35

ACT GAC AAC AAC GGT GCA GTC AAG TTT CCA CAA CTG TGT AAA TTT TGT       497
Thr Asp Asn Asn Gly Ala Val Lys Phe Pro Gln Leu Cys Lys Phe Cys
    40                  45                  50

GAT GTG AGA TTT TCC ACC TGT GAC AAC CAG AAA TCC TGC ATG AGC AAC       545
Asp Val Arg Phe Ser Thr Cys Asp Asn Gln Lys Ser Cys Met Ser Asn
```

-continued

```
         55                   60                    65                    70
TGC AGC ATC ACC TCC ATC TGT GAG AAG CCA CAG GAA GTC TGT GTG GCT              593
Cys Ser Ile Thr Ser Ile Cys Glu Lys Pro Gln Glu Val Cys Val Ala
                75                    80                    85

GTA TGG AGA AAG AAT GAC GAG AAC ATA ACA CTA GAG ACA GTT TGC CAT              641
Val Trp Arg Lys Asn Asp Glu Asn Ile Thr Leu Glu Thr Val Cys His
                90                    95                   100

GAC CCC AAG CTC CCC TAC CAT GAC TTT ATT CTG GAA GAT GCT GCT TCT              689
Asp Pro Lys Leu Pro Tyr His Asp Phe Ile Leu Glu Asp Ala Ala Ser
               105                   110                   115

CCA AAG TGC ATT ATG AAG GAA AAA AAA AAG CCT GGT GAG ACT TTC TTC              737
Pro Lys Cys Ile Met Lys Glu Lys Lys Lys Pro Gly Glu Thr Phe Phe
        120                   125                   130

ATG TGT TCC TGT AGC TCT GAT GAG TGC AAT GAC AAC ATC ATC TTC TCA              785
Met Cys Ser Cys Ser Ser Asp Glu Cys Asn Asp Asn Ile Ile Phe Ser
135                   140                   145                   150

GAA GAA TAT AAC ACC AGC AAT CCT GAC TTG TTG CTA GTC ATA TTT CAA              833
Glu Glu Tyr Asn Thr Ser Asn Pro Asp Leu Leu Leu Val Ile Phe Gln
                155                   160                   165

GTG ACA GGC ATC AGC CTC CTG CCA CCA CTG GGA GTT GCC ATA TCT GTC              881
Val Thr Gly Ile Ser Leu Leu Pro Pro Leu Gly Val Ala Ile Ser Val
                170                   175                   180

ATC ATC ATC TTC TAC TGC TAC CGC GTT AAC CGG CAG CAG AAG CTG AGT              929
Ile Ile Ile Phe Tyr Cys Tyr Arg Val Asn Arg Gln Gln Lys Leu Ser
                185                   190                   195

TCA ACC TGG GAA ACC GGC AAG ACG CGG AAG CTC ATG GAG TTC AGC GAG              977
Ser Thr Trp Glu Thr Gly Lys Thr Arg Lys Leu Met Glu Phe Ser Glu
        200                   205                   210

CAC TGT GCC ATC ATC CTG GAA GAT GAC CGC TCT GAC ATC AGC TCC ACG             1025
His Cys Ala Ile Ile Leu Glu Asp Asp Arg Ser Asp Ile Ser Ser Thr
215                   220                   225                   230

TGT GCC AAC AAC ATC AAC CAC AAC ACA GAG CTG CTG CCC ATT GAG CTG             1073
Cys Ala Asn Asn Ile Asn His Asn Thr Glu Leu Leu Pro Ile Glu Leu
                235                   240                   245

GAC ACC CTG GTG GGG AAA GGT CGC TTT GCT GAG GTC TAT AAG GCC AAG             1121
Asp Thr Leu Val Gly Lys Gly Arg Phe Ala Glu Val Tyr Lys Ala Lys
                250                   255                   260

CTG AAG CAG AAC ACT TCA GAG CAG TTT GAG ACA GTG GCA GTC AAG ATC             1169
Leu Lys Gln Asn Thr Ser Glu Gln Phe Glu Thr Val Ala Val Lys Ile
        265                   270                   275

TTT CCC TAT GAG GAG TAT GCC TCT TGG AAG ACA GAG AAG GAC ATC TTC             1217
Phe Pro Tyr Glu Glu Tyr Ala Ser Trp Lys Thr Glu Lys Asp Ile Phe
        280                   285                   290

TCA GAC ATC AAT CTG AAG CAT GAG AAC ATA CTC CAG TTC CTG ACG GCT             1265
Ser Asp Ile Asn Leu Lys His Glu Asn Ile Leu Gln Phe Leu Thr Ala
295                   300                   305                   310

GAG GAG CGG AAG ACG GAG TTG GGG AAA CAA TAC TGG CTG ATC ACC GCC             1313
Glu Glu Arg Lys Thr Glu Leu Gly Lys Gln Tyr Trp Leu Ile Thr Ala
                315                   320                   325

TTC CAC GCC AAG GGC AAC CTA CAG GAG TAC CTG ACG CGG CAT GTC ATC             1361
Phe His Ala Lys Gly Asn Leu Gln Glu Tyr Leu Thr Arg His Val Ile
        330                   335                   340

AGC TGG GAG GAC CTG CGC AAG CTG GGC AGC TCC CTC GCC CGG GGG ATT             1409
Ser Trp Glu Asp Leu Arg Lys Leu Gly Ser Ser Leu Ala Arg Gly Ile
                345                   350                   355

GCT CAC CTC CAC AGT GAT CAC ACT CCA TGT GGG AGG CCC AAG ATG CCC             1457
Ala His Leu His Ser Asp His Thr Pro Cys Gly Arg Pro Lys Met Pro
                360                   365                   370

ATC GTG CAC AGG GAC CTC AAG AGC TCC AAT ATC CTC GTG AAG AAC GAC             1505
```

```
Ile Val His Arg Asp Leu Lys Ser Ser Asn Ile Leu Val Lys Asn Asp
375                 380                 385                 390

CTA ACC TGC TGC CTG TGT GAC TTT GGG CTT TCC CTG CGT CTG GAC CCT      1553
Leu Thr Cys Cys Leu Cys Asp Phe Gly Leu Ser Leu Arg Leu Asp Pro
                    395                 400                 405

ACT CTG TCT GTG GAT GAC CTG GCT AAC AGT GGG CAG GTG GGA ACT GCA      1601
Thr Leu Ser Val Asp Asp Leu Ala Asn Ser Gly Gln Val Gly Thr Ala
                410                 415                 420

AGA TAC ATG GCT CCA GAA GTC CTA GAA TCC AGG ATG AAT TTG GAG AAT      1649
Arg Tyr Met Ala Pro Glu Val Leu Glu Ser Arg Met Asn Leu Glu Asn
            425                 430                 435

GCT GAG TCC TTC AAG CAG ACC GAT GTC TAC TCC ATG GCT CTG GTG CTC      1697
Ala Glu Ser Phe Lys Gln Thr Asp Val Tyr Ser Met Ala Leu Val Leu
        440                 445                 450

TGG GAA ATG ACA TCT CGC TGT AAT GCA GTG GGA GAA GTA AAA GAT TAT      1745
Trp Glu Met Thr Ser Arg Cys Asn Ala Val Gly Glu Val Lys Asp Tyr
455                 460                 465                 470

GAG CCT CCA TTT GGT TCC AAG GTG CGG GAG CAC CCC TGT GTC GAA AGC      1793
Glu Pro Pro Phe Gly Ser Lys Val Arg Glu His Pro Cys Val Glu Ser
                475                 480                 485

ATG AAG GAC AAC GTG TTG AGA GAT CGA GGG CGA CCA GAA ATT CCC AGC      1841
Met Lys Asp Asn Val Leu Arg Asp Arg Gly Arg Pro Glu Ile Pro Ser
            490                 495                 500

TTC TGG CTC AAC CAC CAG GGC ATC CAG ATG GTG TGT GAG ACG TTG ACT      1889
Phe Trp Leu Asn His Gln Gly Ile Gln Met Val Cys Glu Thr Leu Thr
        505                 510                 515

GAG TGC TGG GAC CAC GAC CCA GAG GCC CGT CTC ACA GCC CAG TGT GTG      1937
Glu Cys Trp Asp His Asp Pro Glu Ala Arg Leu Thr Ala Gln Cys Val
520                 525                 530

GCA GAA CGC TTC AGT GAG CTG GAG CAT CTG GAC AGG CTC TCG GGG AGG      1985
Ala Glu Arg Phe Ser Glu Leu Glu His Leu Asp Arg Leu Ser Gly Arg
535                 540                 545                 550

AGC TGC TCG GAG GAG AAG ATT CCT GAA GAC GGC TCC CTA AAC ACT ACC      2033
Ser Cys Ser Glu Glu Lys Ile Pro Glu Asp Gly Ser Leu Asn Thr Thr
                555                 560                 565

AAA TA GCTCTTATGG GGCAGGCTGG GCATGTCCAA AGAGGCTGCC CCTCTCACCA        2088
Lys

AA                                                                    2090
```

(2) INFORMATION FOR SEQ ID NO:8:

(i) SEQUENCE CHARACTERISTICS:
        (A) LENGTH: 567 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80
```

-continued

```
Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
                180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
                260                 265                 270

Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
    355                 360                 365

Gly Arg Pro Lys Met Pro Ile Val His Arg Asp Leu Lys Ser Ser Asn
    370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
                420                 425                 430

Arg Met Asn Leu Glu Asn Ala Glu Ser Phe Lys Gln Thr Asp Val Tyr
    435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
```

-continued

```
              500                 505                 510
Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
        530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565
```